(12) United States Patent
Stedronsky et al.

(10) Patent No.: US 7,300,663 B2
(45) Date of Patent: *Nov. 27, 2007

(54) ADHESION AND SEALING OF TISSUE WITH COMPOSITIONS CONTAINING POLYFUNCTIONAL CROSSLINKING AGENTS AND PROTEIN POLYMERS

(75) Inventors: Erwin R. Stedronsky, San Clemente, CA (US); Joseph Cappello, San Diego, CA (US)

(73) Assignee: Protein Polymer Technologies, Inc., San Diego, CA (US)

( * ) Notice: Subject to any disclaimer, the term of this patent is extended or adjusted under 35 U.S.C. 154(b) by 47 days.

This patent is subject to a terminal disclaimer.

(21) Appl. No.: 10/117,931

(22) Filed: Apr. 5, 2002

(65) Prior Publication Data

US 2003/0104589 A1    Jun. 5, 2003

Related U.S. Application Data

(63) Continuation of application No. 09/451,206, filed on Nov. 29, 1999, now Pat. No. 6,243,333, which is a continuation of application No. 08/642,246, filed on May 2, 1996, now Pat. No. 6,033,654, and a continuation-in-part of application No. 08/435,641, filed on May 5, 1995, now Pat. No. 5,817,303.

(51) Int. Cl.
- A61L 24/00 (2006.01)
- A61K 31/785 (2006.01)
- C08L 89/00 (2006.01)
- A61F 2/00 (2006.01)
- C07K 1/00 (2006.01)
- C12N 11/00 (2006.01)

(52) U.S. Cl. .................... 424/426; 106/124.1; 424/444; 424/445; 435/174; 514/2; 530/350; 530/402; 530/810

(58) Field of Classification Search ................. 424/423; 106/124.1, 424, 78.02, 78.06; 435/174; 514/2; 530/350, 402, 810

See application file for complete search history.

(56) References Cited

U.S. PATENT DOCUMENTS

| | | | | |
|---|---|---|---|---|
| 4,187,852 A | 2/1980 | Urry et al. | | 128/334 R |
| 4,589,882 A | 5/1986 | Urry | | 633/11 |
| 4,898,926 A | 2/1990 | Urry | | 523/328 |
| 5,064,430 A | 11/1991 | Urry | | 423/1 |
| 5,243,038 A | 9/1993 | Ferrari et al. | | 536/23.1 |
| 5,292,362 A | 3/1994 | Bass et al. | | 106/124 |
| 5,336,256 A | 8/1994 | Urry | | 423/1 |
| 5,374,431 A | 12/1994 | Pang et al. | | 424/486 |
| 5,496,712 A | 3/1996 | Cappello et al. | | 435/69.1 |
| 5,514,581 A | 5/1996 | Ferrari et al. | | 435/252.3 |
| 5,817,303 A | 10/1998 | Stedronsky et al. | | 424/78.02 |
| 6,033,654 A | 3/2000 | Stedronsky et al. | | 424/78.02 |
| 6,423,333 B1 * | 7/2002 | Stedronsky et al. | | 424/423 |

FOREIGN PATENT DOCUMENTS

| | | |
|---|---|---|
| EP | 0 330 344 | 8/1989 |
| JP | 4334396 | 11/1992 |
| WO | WO 93/04711 | 3/1993 |
| WO | WO 94/01508 | 2/1994 |
| WO | WO 95/05396 | 2/1995 |

OTHER PUBLICATIONS

The Condensed Chemical Dictionary, eighth edition, Van Nostrand Reinhold Company, New York, 1971, pp. 230, 737 and. 738.*
Kaleem et al., "Collagen-Based Bioadhesive Varnacle Cement Mimic," Die Angewandte Makromolekulare Chemie, 155:31-43 (1987).

* cited by examiner

*Primary Examiner*—David M. Naff
(74) *Attorney, Agent, or Firm*—Morgan Lewis & Bockius LLP; Richard F. Trecartin

(57) ABSTRACT

Proteinaceous polymers having repetitive units from naturally occurring structural proteins are employed as backbones for functionalities for crosslinking to provide strongly adherent tissue adhesives and sealants. Particularly, block copolymers of elastin and fibroin are employed having lysine substitutions in spaced apart units, where the amino group can be crosslinked using difunctional crosslinking agents.

7 Claims, No Drawings

ADHESION AND SEALING OF TISSUE WITH COMPOSITIONS CONTAINING POLYFUNCTIONAL CROSSLINKING AGENTS AND PROTEIN POLYMERS

CROSS-REFERENCE TO RELATED APPLICATIONS

This application is a continuation of application Ser. No. 09/451,206, filed Nov. 29, 1999, now U.S. Pat. No. 6,423,333, which is a continuation of application Ser. No. 08/642,246, filed May 2, 1996, now U.S. Pat. No. 6,033,654, which is a continuation-in-part of application Ser. No. 08/435,641, filed May 5, 1995, now U.S. Pat. No. 5,817,303.

INTRODUCTION

1. Technical Field

The field of this invention is physiologically acceptable compositions for use as tissue adhesives and sealants.

2. Background

In many situations, there is a need to bond separated tissues. Sutures and staples are effective and well established wound closure devices. However, there are surgical procedures where classical repair procedures are unsatisfactory, limited to highly trained specialists (e.g. microsurgery), or not applicable due to tissue or organ fragility, inaccessibility (e.g. endoscopy procedures), or fluid loss, including capillary "weeping". Tissue adhesives and sealants have been developed to meet these needs. They may be used to seal or reinforce wounds that have been sutured or stapled, as well as finding independent use. The leading commercial products are fibrin glues and cyanoacrylates. However, both products have significant limitations which have prevented their widespread use.

Cyanoacrylates are mainly used for cutaneous wound closure in facial and reconstructive surgery. The appeal of cyanoacrylates is their speed of bonding, which is almost immediate, and its great bond strength. However, its speed of bonding can be a disadvantage, since glued tissue must be cut again in order to reshape it to the desired conformation. Additionally, it can only be used on dry substrates since its mode of action is through a mechanical interlock, limiting its use as a sealant, and it is relatively inflexible compared to surrounding tissue. Cyanoacrylates are also known to be toxic to some tissues and although it is not considered to be biodegradable, potential degradation products are suspected to be carcinogenic.

Fibrin glues comprising blood-derived fibrinogen, factor XIII and thrombin function primarily as a sealant and hemostat and have been used in many different surgical procedures within the body. They have been shown to be non-toxic, biocompatible and biodegradable. They are able to control excessive bleeding and decrease fibrosis. However, tissues bonded with fibrin cannot be subjected to even moderate tensile stress without rupturing the bond. It takes about three to ten minutes for an initial bond to develop, but requires about 30 minutes to several hours for full strength to develop. Depending upon the application, the product may also resorb too quickly. Use of recombinantly produced fibrinogen, factor XIII, thrombin and related components (e.g. fibrin, activated factor XIII) has not been demonstrated to improve the setting time or strength of fibrin glues. Fibrin glues derived from heterologous, human and animal, serum may provoke undesirable immune responses, and expose the patient to the potential risk of viral infection. Autologous fibrin glues may be impractical to obtain and use and may compromise patient safety.

There is, therefore, substantial interest in developing products which have the biocompatibility of fibrin glues, but which set more quickly and have enhanced strength. These products should be readily available, desirably from other than natural sources, be easily administered and capable of resorption over time.

Relevant Literature

Tissue adhesives are described in: Tissue Adhesives in Surgery, Matsumoto, T., Medical Examination Publishing Co., Inc. 1972 and Sierra, D. H., *J. Biomat. App.* 7:309-352, 1993. Methods of preparation of protein polymers having blocks of repetitive units are described in U.S. Pat. No. 5,243,038 and EPA 89.913054.3.

SUMMARY OF THE INVENTION

Polymeric compositions and methods for their use are provided, where the polymeric compositions are capable of in situ chemical crosslinking to provide novel crosslinked polymeric products, which have good mechanical and biological properties, as exemplified by strong adherent bonds to tissue. The compositions can be used in a variety of applications related to their physical, chemical and biological properties, to bond to separated tissue to provide at least one of the characteristics of a stable, flexible, resorbable bond.

DESCRIPTION OF THE SPECIFIC EMBODIMENTS

The subject compositions comprise high molecular weight recombinant polymers having one or a combination of repeating units related to naturally occurring structural proteins. Of particular interest are the repeating units of fibroin, elastin, collagen, and keratin, particularly collagen and combinations of fibroin and elastin. The polymers have functional groups which can be chemically crosslinked under physiological conditions with physiologically acceptable crosslinkers, so as to form a composition which has strong adherent properties to a variety of substrates, has strong mechanical properties in maintaining the joint between the substrates, and can be formulated to have good resorption properties.

Of particular interest, the subject compositions provide strongly adherent bonds to tissue to maintain separated tissue in a contiguous spacial relationship. The subject compositions may also be employed as sealants, where the compositions may serve to fill a defect void in tissue, to augment tissue mass or bond synthetic materials to tissues. The subject compositions may also serve as depots in vivo by being mixed with a drug composition, either when used as an adhesive for bonding tissue together or for other bonding or solely as a slow release source of the drug.

The functionalities for crosslinking may be all the same or combinations of functionalities and may include the functionalities of naturally occurring amino acids, such as amino, e.g. lysine, carboxyl, e.g. aspartate and glutamate, guanidine, e.g. arginine, hydroxyl, e.g. serine and threonine, and thiol, e.g. cysteine. Preferably, the functionality is amino (including guanidine).

The polymers will have molecular weights of at least about 15 kD, generally at least about 30 kD, preferably at least about 50 kD and usually not more than 250 kD, more usually not more than about 150 kD. The polymers will have at least two functionalities, more usually at least about four functionalities, generally having an equivalent weight per functionality in the range of about 1 kD to 40 kD, more usually in the range of about 3 kD to 20 kD, preferably in the range of about 3 kD to 10 kD, there being at least 3, usually at least 6, functionalities available for crosslinking. If desired, one may use mixtures of polymers, where the polymers have combinations of functionalities or have different functionalities present e.g. carboxyl and amino, thiol and aldehyde, hydroxyl and amino, etc. Thus, depending upon the functionalities and the crosslinking agent, one can form amides, imines, ureas, esters, ethers, urethanes, thioethers, disulfides, and the like.

The individual units in the polymer may be selected from fibroin, GAGAGS (SEQ ID NO:01); elastin, GVGVP (SEQ ID NO:02); collagen GXX, where the X's may be the same or different, and at least 10 number % and not more than 60 number % of the X's are proline, and keratin, AKLK/ELAE (SEQ ID NO:3). The desired functionality may be substituted for one of the amino acids of an individual unit or be present as an individual amino acid or part of an intervening group of not more than about 30 amino acids, usually not more than about 16 amino acids. In the former case, within a block of repeats, one or more of the repeats is modified to introduce a crosslinking functionality which would otherwise not normally be present. Thus a valine may be replaced with a lysine, a glycine with an arginine, an alanine with a serine, and the like. In the latter case, there would be an intervening functionality between a block of repeat units, where the number of intervening functionalities would be based on the ranges indicated previously.

Of particular interest are copolymers, either block or random, preferably block, where in the case of elastin and fibroin the ratio of elastin units to fibroin units is in the range of 16-1:1, preferably 8-1:1, where blocks may have different ratios. Normally, in block copolymers, each block will have at least two units and not more than about 32 units, usually not more than about 24 units. By substituting an amino acid in the unit with an amino acid having the appropriate functionality, one can provide for the appropriate number of functionalities present in the polymer or employ intervening groups between blocks.

The individual amino acid repeat units will have from about 3 to 30 amino acids, usually 3 to 25 amino acids, more usually 3 to 15 amino acids, particularly 3 to 12 amino acids, more particularly about 3 to 9 amino acids. At least 40 weight %, usually at least 50 weight %, more usually at least 70 weight %, of the protein polymer will be composed of segments of repetitive units containing at least 2 identical contiguous repetitive units. Generally repeat blocks will comprise at least 2, 4, 7 or 8 units, and combinations thereof, where copolymers are employed, where the unit which is modified with the crosslinking functionality is counted as a unit.

While for the most part, the polymers of the subject invention will have the active functionality of a naturally occurring amino acid in the chain of the polymer, if desired, pendent groups may be employed to provide the desired functionalities. For example, carboxyl groups may be reacted with polyamines so as to exchange a carboxyl functionality for a single amino or plurality of amino groups. An amino group may be substituted with a polycarboxylic acid, so that the amino group will be replaced with a plurality of carboxylic groups. A thiol may be replaced with an aldehyde, by reaction with an aldehydic olefin, e.g. acrolein, so as to provide for an aldehyde functionality.

Other functionalities which may be introduced, if desired, include phosphate esters, activated olefins, e.g. maleimido, thioisocyanato, and the like. The functionalities may be greatly varied from those which naturally occur to provide opportunities for crosslinking. In some instances, this may be desirable to increase the number of functionalities per unit molecular weight, while not increasing the number of functionalities along the chain, for replacing one functionality with another, e.g. thiol with aldehyde, allowing for greater variation in the choice of crosslinking agent.

The crosslinking agent will normally be difunctional, where the functionalities may be the same or different, although higher functionality may be present, usually not exceeding four functionalities. Depending upon the particular functionalities available on the polymers, various crosslinking agents may be employed. The crosslinking agents will usually be at least about three carbon atoms and not more than about 50 carbon atoms, generally ranging from about 3 to 30 carbon atoms, more usually from about 3 to 16 carbon atoms. The chain joining the two functionalities will be at least one atom and not more than about 100 atoms, usually not more than about 60 atoms, preferably not more than about 40 atoms, particularly not more than about 20 atoms, where the atoms may be carbon, oxygen, nitrogen, sulfur, phosphorous, or the like. The linking group may be aliphatically saturated or unsaturated, preferably aliphatic, and may include such functionalities as oxy, ester, amide, thioether, amino, and phosphorous ester. The crosslinking group may be hydrophobic or hydrophilic.

Various reactive functionalities may be employed, such as aldehyde, isocyanate, mixed carboxylic acid anhydride, e.g. ethoxycarbonyl anhydride, activated olefin, activated halo, amino, and the like. By appropriate choice of the functionalities on the protein polymer, and the crosslinking agent, rate of reaction and degree of crosslinking can be controlled.

Various crosslinking agents may be employed, particularly those which have been used previously and have been found to be physiologically acceptable. Crosslinking agents which may be used include dialdehydes, such as glutaraldehyde, activated diolefins, diisocyanates such as, tetramethylene diisocyanate, hexamethylene diisocyanate, octamethylene diisocyanate, acid anhydrides, such as succinic acid dianhydride, ethylene diamine tetraacetic acid dianhydride, diamines, such as hexamethylene diamine, cyclo(L-lysyl-L-lysine), etc. The crosslinking agent may also contain unsymmetrical functionalities, for example, activated olefin aldehydes, e.g. acrolein and quinoid aldehydes, activated halocarboxylic acid anhydride, and the like. The crosslinking agents will usually be commercially available or may be readily synthesized in accordance with conventional ways, either prior to application of the adhesive or by synthesis in situ.

In some instances it may be desirable to react a physiologically acceptable second compound, which serves as a modifying unit, with a polyfunctional, usually bifunctional, compound to change the nature of the crosslinking. The addition of the second compound may be to enhance the rate of crosslinking, change the solubility properties of the crosslinker, enhance or reduce the strength of the crosslinked polymer, enhance or reduce the resorption rate, or provide for other physical, chemical or biological properties of interest. The polyfunctional second compound may be reacted with the crosslinking compound prior to reaction with the protein or concurrently with the reaction with the protein. Where the reaction is prior, the resulting crosslinking product will be physiologically acceptable and when concurrent, the polyfunctional second compound, the crosslinking compound and the resulting crosslinking product will be physiologically acceptable, when used in vivo. The ratio of the polyfunctional second compound to the crosslinking compound will generally be in the range of about 0.1-2:1, more usually in the range of about 0.1-1:1, depending on the reactivity of the polyfunctional second compound when the polyfunctional second compound and crosslinking agent are brought together, the number of crosslinks desired in the final protein composition, the size of the bridge between protein molecules, and the like.

The nature of the polyfunctional second compound may vary widely. The functional groups present may be the same or different from the functional groups present on the polymer, but will be reactive with the functionalities of the crosslinking compound. For example, the polyfunctional second compound may have amino and/or hydroxyl groups, where the protein has amino or hydroxyl functionalities. By employing a diisocyanate with a diol, diurethanes will be produced. Thus, the chain crosslinking the proteins will comprise 2 or more urethanes.

In many instances, the polyfunctional second compound will include an internal functionality that does not participate in the reaction, but provides various other characteristics to the crosslinking agent or the crosslinked protein product. Characteristics of interest include hydrophilicity, hydrolytic instability, sensitivity to enzymatic degradation, biocompatibility, shear strength, and the like. For the most part internal functionalities will comprise oxygen, sulfur and nitrogen atoms, such as ethers, carboxylic acid esters, including urethanes, amino groups, amides, ketones, dithiols and the like. To enhance the rate of resorption, ester groups are of interest, while to enhance hydrophilicity, the same groups maybe employed as well as ethers, such as polyoxyalkylene groups.

The polyfunctional second compound will generally have at least 2 carbon atoms and not more than 50 carbon atoms, usually not more than about 30 carbon atoms, desirably having not more than about 16 carbon atoms per heteroatom. Naturally occurring or synthetic bifunctional compounds may be employed. Illustrative compounds include lysine, arginine, di-(2'-aminoethyl) malonate, citrate, lysyl lysine, 2'-aminoethyl glycinate, O, N-diglycinyl ethanolamine, diethylene glycol diglycinate, cystine, and the like. To provide terminal amino groups, various low molecular weight amino acids may be used, particularly glycine and alanine bonded to an intervening difunctional compound, such as ethylene glycol, diethylene glycol, and tetraethylene glycol, propanediol, 1,4-butyn-2-diol, ascorbic acid, etc.

The subject compositions may be prepared prior to the use of the adhesive by combining the protein polymer and the crosslinking agent, where one or both may have extenders. The two compositions may be readily mixed in accordance with conventional ways, for example, using syringes which can inject the ingredients into a central reactor and the mixture mixed by drawing the mixture back into the syringes and moving the mixture back and forth. Alternatively, the two compositions may be dispensed simultaneously at the site of application. In some instances it may be desirable to allow the crosslinking agent to partially react with the protein prior to adding the polyfunctional second compound. Alternatively, one may mix the polyfunctional second compound with the protein prior to mixing with the crosslinking agent.

Usually, the polymer will be available as a dispersion or solution, particularly aqueous, generally the concentration of the protein polymer being in the range of about 50 mg to 1 g/ml, more usually from about 100 to 800 mg/ml. The solution may be buffered at a pH which enhances or retards the rate of crosslinking. Usually the pH will be in the range of about 2 to 12, more usually 8 to 11. Various buffers may be used, such as phosphate, borate, carbonate, etc. The cation can have an effect on the nature of the product, and to that extent, the alkali metals potassium and sodium, are preferred. The protein composition will generally be about 5 to 40, more usually from about 5 to 20, preferably from about 10 to 20 weight %, to provide for a composition which may be readily handled, will set up within the desired time limit, and the like. The buffer concentration will generally be in the range of about 50 to 500 mM. Other agents may be present in the protein solution, such as stabilizers, surfactants, and the like. If the polyfunctional second compound is present, its concentration will be determined in accordance with its ratio to the crosslinking agent and the polymer.

The ratio of crosslinking agent to polymer will vary widely, depending upon the crosslinking agent, the number of functionalities present on the polymer, the desired rate of curing, and the like. Generally, the weight ratio of polymer to crosslinking agent will be at least about 1:1 and not greater than about 100:1, usually not greater than about 50:1, generally being in the range of about 2 to 50:1, but in some instances may not be more than 30:1. The equivalent ratio of protein to crosslinking agent will generally be in the range of about 0.1-1:3, more usually in the range of about 0.5-2:2. Considerations in selecting the protein-crosslinking agent equivalent ratio will be the rate of setup, reactivity of the crosslinking agent, relative solubility of the crosslinking agent in the mixture, physiological properties of the crosslinking agent, desired degree of stability of the crosslinked product, and the like.

If desired, various extenders or extending agents may be used, particularly naturally occurring proteins. Such extenders will usually not exceed 50 weight percent of the composition, generally not exceeding about 20 weight percent, more usually not exceeding about 10 weight percent. Extenders which may be employed include, but are not limited to: synthetic polymers, both addition and condensation polymers, both protein and non-protein, such as polylactides, polyglycolides, polyanhydrides, polyorthoesters, polyvinyl compounds, polyolefins, polyacrylates, polyethylene glycol, polyesters, polyvinyl alcohol, polyethers, copolymers and derivatives thereof; and naturally occurring polymers, such as proteins and non-proteins, including collagen, fibrinogen, fibronectin, laminin, keratin, chitosan, heparin, dextran, alginates, cellulose, glycosoaminoglycans, hyaluronic acid, polysaccharides, derivatives thereof, and the like. The extenders may modulate the setting time and provide for desirable physical or physiological properties of the adhesive.

Based on the lap shear tensile strength test described in the experimental section, within 30 minutes, usually within 15 minutes, more usually within 5 minutes, the lap shear tensile strength will be at least 100, preferably at least about 250, more preferably at least about 300, usually not exceeding about 4000, more usually not exceeding about 3000 g/cm$^2$.

The subject compositions may be applied to the tissue in any convenient way, for example by using a syringe, catheter, cannula, manually applying the composition, spraying or the like. The subject compositions may be applied to the tissue prior to or during the time the tissue segments are held in contiguous relationship. The subject compositions will rapidly develop substantial shear strength, so as to maintain the tissue in proximity. In some situations there will be an interest in having the composition decompose after some reasonable period of time, usually at least one week and generally not more than about four weeks.

Tissues of interest include vascular vessels such as an artery, vein or capillary, muscel, nerve, organs, e.g. liver, spleen, etc., lung, dura, colon, and the like.

In addition to their use as adhesives, the subject compositions may be used to seal or fill defects, e.g. voids or holes, in tissue, and therefore find use as sealants. Thus, the compositions may serve to stop or staunch the flow of fluid, e.g. blood, through ruptured vessels, e.g. arteries, veins, capillaries and the like. In using the subject compositions as sealants, the composition will be applied, as described above, at the site of the defect, whereby it will set and seal the defect. The compositions may be injected into normal or abnormal tissues to augment the tissue mass, e.g. dermis.

The subject compositions may also find use in the formation of articles of manufacture, by themselves or in combination with other materials. In one application, articles may be produced for use internally to a mammalian host, where there is an interest in biocompatibility, reabsorption rate, ability to vascularize, tissue adhesive and/or bonding capability, and the like. Various articles can be prepared, such as gels, films, threads, coatings, formed objects such as pins and screws, or injectable compositions which are flowable, where the injectable composition may set up and bond or seal tissues, form a depot for a drug, augment tissue or be a filler, coating or the like. The formed objects may be prepared in accordance with conventional ways, such as molding, extrusion, precipitation from a solvent, solvent evaporation, and the like. The flowable depot can be obtained by using a molecular dispersion, fine particles in a medium saturated with a polymer, using a melt, where the melting temperature may be achieved by adding physiologically acceptable additives, and the like.

The articles may find use in a variety of situations associated with the implantation of the article into a mammalian host or the application of the article to the surface of a mammalian host, e.g. wound healing, burn dressing, etc. Those situations, where the performance of the articles may be retained for a predetermined time and replaced by natural materials through natural processes, desirably employ materials which will be resorbed after having fulfilled their function in maintaining their role until the natural process has reestablished a natural structure. Thus, the compositions may find use in holding tissue together, covering tissue, encapsulating cells for organs, providing a coating that cells can invade and replace the composition with natural composition, e.g., bone, soft tissues and the like.

To enhance the rate of curing of the polymeric composition, the composition may be partially prepolymerized. When prepolymerized, the polymer will usually have at least about 3% of the total number of crosslinks and not more than about 75% of the total number of crosslinks, as compared to completion of the crosslinking action. The number of crosslinks should allow the resulting product to be workable and provide sufficient time prior to set up for it to be manipulated and used. Alternatively, one may react the functional groups with an excess of the crosslinking reagent, so that the effect is to substitute the functionality of the protein with the functionality of the crosslinking agent. The protein with the substituted functionality may then be used to crosslink protein with the original functionality or with a polyfunctional second compound.

The subject compositions may also be used as depots to provide for a relatively uniform release of a physiologically active product, e.g., a drug. The drug may be mixed with a subject composition at an appropriate concentration prior to crosslinking. As the crosslinked polymer is degraded, the drug will be released due to diffusion as well as erosion of the external surface of the depot. By controlling the form or shape of the depot, the degree of crosslinking, the concentration of the drug and the like, a physiologically therapeutic level of the drug may be maintained over extended periods of time. The period required for absorption can be as short as 0.5 day and may exceed 4, 6 or 8 weeks or more, depending upon the particular composition and the application.

The protein polymer compositions may be prepared in accordance with conventional ways. See, for example, U.S. Pat. No. 5,243,038, which disclosure is incorporated herein by reference. Briefly, sequences may be synthesized comprising a plurality of repeating units, where complementary sequences result in dsDNA having overhangs. A series of dsDNA molecules may be prepared and stepwise introduced into a cloning vector as the gene for the protein is constructed. A monomer can be obtained in this way, which may be sequenced to ensure that there have been no changes in the sequence, followed by multimerization of the monomer, cloning and expression. For further details, see the above indicated patent.

The following examples are offered by way of illustration and not by way of limitation.

EXPERIMENTAL

EXAMPLE 1

Methods

The construction of synthetic DNA and its use in large polypeptide synthesis is described in U.S. Pat. No. 5,243,038; PCT/US89/05016 and PCT/US92/09485, the disclosures of which are herein incorporated by reference. Modifications to these methods and additional methods used are described below.

1. Use of Filters and Columns for DNA Purification
　A. Ultrafree®-Probind filter unit ("Probind", Millipore): the DNA containing solution was applied to the filter unit and spun at 12,000 RPM for 30 seconds in a Sorvall Microspin 24S.
　B. Microcon-30 filter (Amicon): the DNA containing solution was washed by applying to the filter and exchanging twice with $H_2O$ by spinning at 12,000 RPM for 6 minutes in a microfuge.
　C. Bio-Spin 6 column ("Bio-Spin", BioRad): Salts and glycerol were removed from the DNA solution by applying to the column, previously equilibrated in TEAB (triethyl ammonium bicarbonate pH 7.0), and spinning in a Sorvall RC5B centrifuge using an HB4 rotor at 2,500 RPM for 4 minutes.

2. Phosphatase Treatment of DNA

Phosphatase treatment of DNA was also performed by resuspending ethanol precipitated DNA from the restriction enzyme digest in 20 mM Tris-HCl pH 8.0, 10 mM $MgCl_2$ to a final DNA concentration of 20 μg/ml. Shrimp Alkaline Phosphatase (SAP) was added at 2 U/μg of DNA and the mixture was incubated at 37° C. for one hour, heat inactivated for 20 minutes at 65° C. and then passed through a Probind filter and subsequently a Bio-Spin column.

3. Preparative Agarose Gel Electrophoresis

For agarose ligation, the buffer used was 1× TAE (50 mM Tris-acetate, pH 7.8).

4. Agarose DNA Ligation

The agarose was melted at 65° C., the temperature was then lowered to 37° C. and ligation buffer (5×=100 mM Tris-HCl, pH 7.5, 50 mM $MgCl_2$, 50 mM DTT, 1 mM ATP) was added; the tube was then placed at room temperature and ligase was added (1000 units T4 DNA ligase (NEB)). The reaction volume was usually 50 µl. The reaction was incubated at 15° C. for 16-18 hours.

5. Agarose DNA Purification Using an Ultrafree®-MC Filter Unit

This procedure can be used for agarose slices up to 400 µl in size. After agarose gel electrophoresis, the DNA is visualized by ethidium bromide staining and the agarose block containing the DNA band of interest is excised. The agarose is then frozen at −20° C. for 1 hour, then quickly thawed at 37° C. for 5 minutes. The agarose is then thoroughly macerated. The pieces are then transferred into the sample cup of the filter unit and spun at 5,000× g in a standard microfuge for 20 minutes. The agarose is then resuspended in 200 µl of Tris-EDTA, or other buffer, and incubated at room temperature for 30 minutes to allow for elution of additional DNA from the gel. The mixture is then centrifuged for an additional 20 minutes at 10,000 RPM. The DNA is, at this point, in the filtrate tube separated from the agarose fragments and ready for subsequent DNA manipulations.

6. Preparation of Antibody to Artificially Synthesized Peptides

The same procedures were used as described in U.S. Pat. No. 5,243,038, PCT/IUS89/05016 and PCT/US92/09485.

7. Immunoblotting of Proteins in Gels

An alternative to the $^{125}$I-Protein A detection method was used. This method relied on a chemiluminescent signal activated by horseradish peroxidase (HRP). The chemiluminescent reagents are readily available from several suppliers such as Amersham and DuPont NEN. The western blot was prepared and blocked with BLOTTO. A number of methods were used to introduce the HRP reporter enzyme including, for example, a hapten/anti-hapten-HRP, a biotinylated antibody/streptavidin-HRP, a secondary reporter such as a goat or mouse anti-rabbit IgG-biotinylated/streptavidin-HRP, or a goat or mouse-anti rabbit IgG-HRP. These reagents were bought from different sources such as BioRad or Amersham and occasionally biotinylated antibodies were prepared in our laboratory using Biotin NHS from Vector Laboratories, Burlingame, Calif. (Cat. #SP-1200) following the procedure accompanying the product. The following is an example of a procedure used to detect the expression of protein polymers.

The blot was placed in 15 ml of BLOTTO solution containing biotinylated goat anti-rabbit IgG (BioRad) diluted in BLOTTO (1:7500) and gently agitated for 2 hours at room temperature. The filter was then washed for 30 minutes with 3 changes of TSA (50 mM Tris-HCl pH 7.4, 0.9% NaCl, 0.2% sodium azide) and then for 5 minutes each in TBS with 0.1% TWEEN®20. The blot was then incubated for 20 minutes at room temperature with gentle rotation, in 20 ml of TBS (100 mM Tris Base, 150 mM NaCl, pH 7.5) HRP-Streptavidin (Amersham) diluted 1:1000 in TBS with 0.1% Tween 20. The blot was then washed three times for 5 minutes each in TBS with 0.3% Tween 20 and then three times for 5 minutes each in TBS with 0.1% Tween 20. The blot was then incubated for 1 minute with gentle agitation in 12 ml of development solutions #1 an #2 (Amersham) equally mixed. The blot was removed from the development solution and autoradiographed.

8. Protein Expression Analysis

An overnight culture which had been grown at 30° C. was used to inoculate 50 ml of LB media contained in a 250 ml flask. Kanamycin was added at a final concentration of 50 µg per ml and the culture was incubated with agitation (200 rpm) at 30° C. When the culture reached an $OD_{600}$ of 0.8, 40 ml were transferred to a new flask prewarmed at 42° C. and incubated at the same temperature for approximately 2 hours. The cultures (30° and 42°) were chilled on ice and $OD_{600}$ was taken. Cells were collected by centrifugation and then divided in 1.0 $OD_{600}$ aliquots and used to perform western analysis using the appropriate antibodies.

9. Amino Acid Analysis

Amino acid derivatives were analyzed by reverse phase HPLC using a Waters 600E system.

10. Peptide Synthesis

Synthetic peptides were also prepared on a Rainin/Protein Technologies PS3 FMOC peptide synthesizer. Both the synthesis and cleavage were accomplished using the methods supplied by the manufacturer in the instrument manual.

11. In vitro DNA Synthesis

The β-cyanoethyl phosphoramidites, controlled-pore glass columns and all synthesis reagents were obtained from Applied Biosystems, Foster City, Calif. Synthetic oligonucleotides were prepared by the phosphite triester method with an Applied Biosystems Model 381A DNA synthesizer using a 10-fold excess of protected phosphoramidites and 0.2 µmole of nucleotide bound to the synthesis support column. The chemistries used for synthesis are the standard protocols recommended for use with the synthesizer and have been described (Matteucci et al., *J. Amer. Chem. Soc.*, 103:3185-3319 (1981)). Deprotection and cleavage of the oligomers from the solid support were performed according to standard procedures as provided by Applied Biosystems. The repetitive yield of the synthesis as measured by the optical density of the removed protecting group as recommended by Applied Biosystems was greater than 97.5%.

The crude oligonucleotide mixture was purified by preparative gel electrophoresis as described by the Applied Biosystems protocols in Evaluating and Isolating Synthetic Oligonucleotides, 1992 (Formerly: User Bulletin 13, 1987). The acrylamide gel concentration varied from 10 to 20% depending upon the length of the oligomer. If necessary, the purified oligomer was identified by UV shadowing, excised from the gel and extracted by the crush and soak procedure (Smith, *Methods in Enzymology*, 65:371-379 (1980)).

For DNA synthesis of oligonucleotides longer then 100 bases, the synthesis cycle was changed from the protocol recommended by Applied Biosystems for the 381A DNA synthesizer. All the reagents used were fresh. All the reagents were supplied by Applied Biosystems except for the acetonitrile (Burdick and Jackson Cat #017-4 with water content less then 0.001%) and the 2000 Å pore size column (Glen Research). Due to the length of the oligo, interrupt pauses had to be inserted during the synthesis to allow changing the reagent bottles that emptied during synthesis. This interrupt pause was done at the cycle entry step and the pause was kept as short as possible. The washes after detritylation by TCA, through the beginning of each synthesis cycle, were increased from about 2× to 3× over the recommended time. The time allocated for the capping was also increased to limit truncated failure sequences. After the synthesis the deprotection was done at 55° C. for 6 hours. After desalting the synthesized DNA was amplified using PCR.

12. Sequencing of DNA

Storage and analysis of data utilized software from DNA Strider, DNA Inspection IIe or DNAid for Apple Macintosh personal computer.

13. Dideoxy DNA sequencing of double stranded plasmid DNA

As described in U.S. Pat. No. 5,243,038, plasmid DNA was prepared on a small scale. Primers were synthesized using a DNA synthesizer and were annealed to the plasmid DNA following the procedure described for M13 sequencing. The sequencing reactions were done using Sequenase (United States Biochemicals) and the conditions were as recommended by the supplier. All sequences were run on polyacrylamide gels.

14. PCR Amplification

The PCR reaction was performed in a 100 µl volume in a Perkin Elmer thin-walled Gene Amp™ reaction tube. Approximately 1 µM of each primer DNA was added to 1× PCR buffer (supplied by Perkin Elmer as 10× solution), 200 µM of each dNT, 5U AmpliTaq, and several concentrations of the target DNA. Amplification was performed in a Perkin Elmer DNA Thermal cycler model 480 for 30 cycles with the following step cycles of 12 minutes each: 95° C., 62° C., and 72° C. Aliquots from the different reactions were analyzed by agarose gel electrophoresis using 1.5% low melting point agarose in 0.5× TA buffer. The reaction mixtures that gave the desired band were pooled and spun through a Probind filter to remove the AmpliTaq enzyme, then a Microcon-30 filter and a Bio-Spin column. The DNA was then concentrated in vacuo.

15. Diamine Synthesis

2-Aminoethyl Glycinate:

Concentrated sulfuric acid (9.90 g, 0.101 mole) was diluted into 10 mL of water. Glycine (7.50 g, 0.100 mole), 2-aminoethanol (6.10 g, 0.100 mole) and the diluted sulfuric acid were placed in a 250 mL, 3-neck, round bottom flask fitted with a stopper, a mechanical stirrer, a heating mantle, and a Dean-Stark water trap. The contents of the apparatus were protected from atmospheric moisture with a nitrogen blanket. Toluene (100 mL) was added and the contents of the apparatus refluxed until no further evolution of water occurred. The apparatus was disassembled and the toluene was decanted before the flask was connected to a vacuum line to strip off toluene entrapped in the reaction mass. The product was used without further purification. The FTIR spectrum of the reaction product shows strong carbonyl adsorptions at 1736 cm$^{-1}$ and 1672 cm$^{-1}$. The reaction product is estimated to be an approximately 4:1 mixture of 2-aminoethyl glycinate and N,O-diglycyl ethanolamine by comparison with the spectra of ethyl glycinate hydrochloride and glycyl glycine hydrochloride.

Cholinyl Lysinate:

Concentrated sulfuric acid (11.40 g, 0.120 mole) was diluted into water (10 mL). Lysine monohydrochloride (13.69 g, 0.075 mole), choline chloride (10.47 g, 0.075 mole), and the diluted sulfuric acid was placed into a 250 mL 1-neck round bottom flask fitted with a magnetic stirring bar, heated in a thermostatted oil bath, and connected to a vacuum line. Vacuum was gradually applied to the flask and then heat gradually increased in order to remove volatiles into a trap cooled in liquid nitrogen. The reaction was terminated when the bath temperature reached 110° C. and the pressure decreased to 0.024 mm-Hg. The product is homogeneous by thin layer chromatography (cellulose, acetic acid/acetonitrile/water 5:65:30 v/v/v, developed with ninhydrin spray, Rf=0.25). The product was used directly.

1,3-Propanediyl Diglycinate:

Concentrated sulfuric acid (10.78 g, 0.110 mole) was diluted into water (10 mL). 1,3-Propanediol (7.61 g, 0.100 mole), glycine (15.0 g, 0.200 mole), and the diluted sulfuric acid were placed in a 250 mL, 3-neck, round bottom flask fitted with a stopper, a mechanical stirrer, a thermostatted oil bath, and a Dean-Stark water trap. The contents of the apparatus were protected from atmospheric moisture with a nitrogen blanket. Toluene (100 mL) was added, the oil bath thermostatted at 130° C., and the contents of the apparatus refluxed until no further evolution of water occurred (ca. 9 hours). The apparatus was disassembled and the toluene decanted. The reaction mass was dissolved in water (29 mL) by stirring at room temperature. Upon cooling to −20° C. for 18 hours, the solution deposits fine white crystals which are removed by filtration. The filtrate is poured into methanol (250 mL), precooled to 3° C., to deposit a semi-solid paste. The supernatant was decanted, and the paste triturated in several portions in a mortar and pestle with methanol (50 mL) to yield a granular solid (12.55 g). A sample of solid (9.19 g) was boiled with methanol (18.4 mL) plus water (7.9 mL), filtered while hot, and allowed to crystallize at 4° C. for 18 hours. The precipitate was filtered while cold, compacted on the funnel under a dam, rinsed with methanol, acetone, and air dried, to yield a white crystalline solid (6.89 g). A sample of this material was titrated with aqueous KOH using a pH meter. The apparent equivalent weight per amine is 201 g/mole; an acidic contaminant with an apparent equivalent weight of 601 g/mole was also present. The FTIR shows a single carbonyl absorption at 1744 cm$^{-1}$.

16. Fermentation Conditions

The fermentors used for the expression of protein polymers were usually a 15 L MBR, 10 L working volume, or a 13 L Braun Biostat E, 8.5 L working volume. The choice of the fermentor and its size is not critical. Any media used for the growth of E. coli can be used. The nitrogen source ranged from NZAmine to inorganic salts and the carbon source generally used was glycerol or glucose. All fermentations were done with the appropriate selection conditions imposed by the plasmid requirements (e.g. kanamycin, ampicillin, etc.). The fermentation method used to express protein polymers in E. coli was the fed-batch method. This is the preferred method for the fermentation of recombinant organisms even if other methods can be used.

The fed-batch method exploits the stage of cell growth where the organisms make a transition from exponential to stationary phase. This transition is often the result of either depletion of an essential nutrient or accumulation of a metabolic byproduct. When the transition is the result of nutrient depletion, the addition of nutrients to the system causes cell division to continue. One or more essential nutrients can incrementally be added to the fermentation vessel during the run, with the net volume increasing during the fermentation process. The result is a controlled growth rate where biomass and expression levels can be optimized. When the cell number in the culture has reached or is approaching a maximum, protein polymer production is induced by providing an appropriate physical or chemical signal, depending upon the expression system used. Production will then continue until the accumulated product reaches maximum levels (Fiestchko, J., and Ritch, T., Chem. Eng. Commun. 1986, 45:229-240; Seo, J. H.; Bailey, J. E., Biotechnol. Bioeng. 1986, 28:1590-1594).

EXAMPLE 2

Construction of SELP8K, SELP8E and CLP6

Polymers were prepared designated SELP8K and SELP8E, which are characterized by having functional groups for cross-linking. The construction of these polymers is described below starting from the previous gene monomer, SELP0 (see U.S. Pat. No. 5,243,038, pSY1298).

SELP8K and SELP8E Amino Acid Monomer Sequence Design:

SELP8K MONOMER (GAGAGS)$_4$ (GVGVP)$_4$ GKGVP (GVGVP)$_3$ (SEQ ID NO:04)

SELP8E MONOMER (GAGAGS)$_4$ (GVGVP)$_4$ GEGVP (GVGVP)$_3$ (SEQ ID NO:05)

SELP8 Construction

Plasmid pSY1378 (see U.S. Pat. No. 5,243,038) was digested with BanI REN, purified using agarose gel electrophoresis followed by NACS colunm, and the DNA was then ethanol precipitated in 2.5 M ammonium acetate and ligated with pPT0134 (See PCT\US92\09485) previously digested with FokI REN, phenol/chloroform extracted and ethanol precipitated.

The products of the ligation mixture were transformed into E. coli strain HB101. Plasmid DNA from transformants was purified and analyzed by digestion using NruI and XmnI RENs. Plasmid pPT0255 containing the desired restriction pattern was obtained and was used for subsequent constructions.

Plasmid DNA pPT0255 was treated with Cfr10I REN followed by RNAse. The digestion fragments were separated by agarose gel electrophoresis, the DNA was excised and self-ligated. The products of the ligation mixture were transformed into E. coli strain HB101. Plasmid DNA from transformants was purified and analyzed by digestion using NaeI and StuI RENs. Plasmid pPT0267 containing the desired deletion was used for subsequent constructions.

Two oligonucleotide strands as shown in Table 1 were synthesized and purified as described in Example 1.

TABLE 1

(SEQ ID NO:06)
5'-CTGGAGCGGGTGCCTGCATGTACATCCGAGT-3'

(SEQ ID NO:07)
3'-CCGAGACCTCGCCCACGGACGTACATGTAGGCTCA-5'

The two oligonucleotide strands were annealed and ligated with the DNA of plasmid pPT0267 which had been previously digested with BanII and ScaI RENs, and purified by agarose gel electrophoresis followed by NACS column.

The products of this ligation reaction were transformed into E. coli strain HB101. Plasmid DNA from transformants was purified and digested with DraI. Plasmid DNA from two clones that gave the correct digestion pattern was sequenced. One plasmid DNA, designated pPT0287, was found to be correct and chosen for further constructions.

Plasmid DNA pSY1298 (see U.S. Pat. No. 5,243,038) was digested with BanII REN, and the SELP0 gene fragment was purified by agarose gel electrophoresis followed by NACS and then ligated to pPT0287 digested with BanII. The enzyme was then removed using phenol/chloroform extraction and ethanol precipitation.

The products of the ligation mixture were transformed into E. coli strain HB101. Plasmid DNA from transformants was purified and analyzed by digestion using DraI REN. Plasmid DNA from the clones showing the correct restriction pattern was further digested with BanII, AhaII and StuI RENs. Plasmid pPT0289 contained the desired SELP8 monomer sequence (see Table 2).

TABLE 2

SELP8 Gene Monomer Sequence (SEQ ID NOS:08 & 09)

```
BanI                          BanII
GGT GCC GGT TCT GGA GCT GGC GCG GGC TCT GGA GTA
CCA CGG CCA AGA CCT CGA CCG CGC CCG AGA CCT CAT
 G   A   G   S   G   A   G   A   G   S   G   V

GGT GTG CCA GGT GTA GGA GTT CCG GGT GTA GGC GTT
CCA CAC GGT CCA CAT CCT CAA GGC CCA CAT CCG CAA
 G   V   P   G   V   G   V   P   G   V   G   V

CCG GGA GTT GGT GTA CCT GGA GTG GGT GTT CCA GGC
GGC CCT CAA CCA CAT GGA CCT CAC CCA CAA GGT CCG
 P   G   V   G   V   P   G   V   G   V   P   G

SmaI
GTA GGT GTG CCC GGG GTA GGA GTA CCA GGG GTA GGC
CAT CCA CAC GGG CCC CAT CCT CAT GGT CCC CAT CCG
 V   G   V   P   G   V   G   V   P   G   V   G

GTC CCT GGA GCG GGT GCT GGT AGC GGC GCA GGC
CAG GGA CCT CGC CCA CGA CCA TCG CCG CGT CCG
 V   P   G   A   G   A   G   S   G   A   G

BanII
GCG GGC TCT GGA GCG
CGC CCG AGA CCT CGC
 A   G   S   G   A
```

Construction of SELP8K and SELP8E Gene Monomers

One oligonucleotide strand coding for a portion of the SELP8 gene monomer was synthesized with a single base polymorphism at position 90. The use of both adenine and guanidine at this position produced oligonucleotides from a single synthesis that encoded the amino acids lysine and glutamic acid (see Table 3). The synthesis was conducted using an Applied Biosystems DNA synthesizer model 381A and a 2000 Å synthesis column supplied by Glen Research. During the synthesis the required interrupt-pauses for bottle changes were minimized. After the synthesis the 202 base DNA fragment was deprotected and cleaved from the column support by treatment in 30% ammonium hydroxide at 55° C. for 6 hours.

TABLE 3

(SEQ ID NO:10)
5'-ATGGCAGCGAAAGGGGACCGGGCTCTGGTGTTGGAGTGCCAGGTGTC

GGTGTTCCGGGTGTAGGCGTTCCGGGAGTTGGTGTACCTGGA(A/G)AAG

GTGTTCCGGGGGTAGGTGTGCCGGGCGTTGGAGTACCAGGTGTAGGCGTC

CCGGGAGCGGGTGCTGGTAGCGGCGCAGGCGCGGGCTCTTTCCGCTAAAG

TCCTGCCCGT-3'

Two additional DNA strands were used as primers for PCR amplification. The two strands were:
1. 5'-AAGAAGGAGATATCATATGGCAGC-GAAAGGGGACC-3' (SEQ ID NO:11)
2. 5'-CGCAGATCTTTAAATTACGGCAGGACTT-TAGCGGAAA-3' (SEQ ID NO:12)

The PCR reaction was carried out and the reaction product was purified as described in Example 1.

The DNA was resuspended and digested with BanII REN as described in Example 1. The digested DNA was then separated by low-melting agarose gel electrophoresis and ligated with pPT0289 previously digested with BanII RENs and purified by NACS column. The products of the ligation reaction were transformed into *E. coli* strain HB101. Plasmid DNA from isolated transformants was purified and analyzed by digestion using ApaLI and EcoNI RENs. Plasmid DNA from the clones showing the correct restriction pattern were further analyzed by digestion using Asp700 REN to distinguish between clones encoding a lysine or glutamic acid at the polymorphic position. Plasmid DNA from clones containing each of the polymorphs was purified and analyzed by DNA sequencing. Plasmid pPT0340 contained the desired SELP8K monomer sequence (see Table 4) and pPT0350 contained the desired SELP8E monomer sequence.

TABLE 4

SELP8K Gene Monomer Sequence (SEQ ID NO:13 &14)

```
BanI                              BanII
GGT GCC GGT TCT GGA GCT GGC GCG GGC TCT GGT GTT
CCA CGG CCA AGA CCT CGA CCG CGC CCG AGA CCA CAA
G   A   G   S   G   A   G   A   G   S   G   V

GGA GTG CCA GGT GTC GGT GTT CCG GGT GTA GGC GTT
CCT CAC GGT CCA CAG CCA CAA GGC CCA CAT CCG CAA
G   V   P   G   V   G   V   P   G   V   G   V

EcoNI
CCG GGA GTT GGT GTA CCT GGA AAA GGT GTT CCG GGG
GGC CCT CAA CCA CAT GGA CCT TTT CCA CAA GGC CCC
P   G   V   G   V   P   G   K   G   V   P   G

GTA GGT GTG CCG GGC GTT GGA GTA CCA GGT GTA GGC
CAT CCA CAC GGC CCG CAA CCT CAT GGT CCA CAT CCG
V   G   V   P   G   V   G   V   P   G   V   G.

SmaI
GTC CCG GGA GCG GGT GCT GGT AGC GGC GCA GGC
CAG GGC CCT CGC CCA CGA CCA TCG CCG CGT CCG
V   P   G   A   G   A   G   S   G   A   G
```

TABLE 4-continued

SELP8K Gene Monomer Sequence

```
  BanII
GCG GGC TCT GGA GCG
CGC CCG AGA CCT CGC
A   G   S   G   A
```

SELP8K Polymer Construction

Plasmid DNA from pPT0340 was digested with BanI REN and the digestion fragments were separated by agarose gel electrophoresis. The SELP8K gene fragment, 192 bp, was excised and purified by NACS column. The purified fragment was ligated with plasmid pPT0317 which had been digested with BanI REN, passed through a Millipore Probind and a Bio-Spin 6 column. The DNA was then treated with shrimp alkaline phosphatase (SAP) as described in Example 1.

The products of this ligation reaction were transformed into *E. coli* strain HB101. Transformants were selected for resistance to kanamycin. Plasmid DNA from individual transformants was purified and analyzed for increase size due to SELP8K monomer multiple DNA insertion. Several clones were obtained with insert sizes ranging from 200 bp to approximately 7 kb. Clones containing from 6 to 32 repeats, were used for expression of the SELP8K protein polymer (pPT0341, pPT0343, pPT0344, pPT0345 and pPT0347).

SELP8K Expression Analysis

An overnight culture which had been grown at 30° C. was used to inoculate 50 ml of LB media contained in a 250 ml flask. Kanamycin was added at a final concentration of 50 μg per ml and the culture was incubated with agitation (200 rpm) at 30° C. When the culture reached an $OD_{600}$ of 0.8, 40 ml were transferred to a new flask prewarmed at 42° C. and incubated at the same temperature for approximately 2 hours. The cultures (30° and 42°) were chilled on ice and $OD_{600}$ was taken. Cells were collected by centrifugation and divided in 1.0 $OD_{600}$ aliquots and used to perform western analysis using anti-SLP antibody.

*E. coli* strain HB101 containing plasmids pPT0341, pPT0343, pPT0344, pPT0345 and pPT0347 were grown as described above. The proteins produced by these cells were analyzed by Western blot for detection of proteins reactive to SLP antibodies. Each clone produced a strongly reactive band. The apparent molecular weights of the products ranged from approximately 35 kD to greater than 250 kD. Strain pPT0345 produced an SLP antibody reactive band of apparent molecular weight 80,000. The expected amino acid sequence of the SELP8K polymer encoded by plasmid pPT0345 is shown below.

pPT0345  SELP8K  884 AA  MW 69,772

MDPVVLQRRDWENPGVTQLNRLAAHPPFASDPMGAGSGAGAGS  (SEQ ID NO:15)

[ (GVGVP)$_4$ GKGVP (GVGVP)$_3$ (GAGAGS)$_4$ ]$_{12}$ (GVGVP)$_4$ GKGVP (GVGVP)$_3$ (GAGAGS)$_2$

GAGAMDPGRYQDLRSHHHHHH

SELP8K Purification

SELP8K was produced in *E. coli* strain pPT0345 by fermentation. The product was purified from the cellular biomass by means of cellular lysis, clearance of insoluble debris by centrifugation, and affinity chromatography. The purified product was analyzed by sodium dodecyl sulfate polyacrylamide gel electrophoresis, immunoreactivity with a polyclonal antisera which reacts with silk-like peptide blocks (SLP antibody), and amino acid analysis. A protein band of apparent molecular weight 80,000 was observed by amido black staining of SDS-PAGE separated and transferred samples and the same band reacted with the SLP antibody on Western blots. As expected, amino acid analysis (shown in Table 5) indicated that the product was enriched for the amino acids glycine (43.7%), alanine (12.3%), serine (5.3%), proline (11.7%), and valine (21.2%). The product also contained 1.5% lysine. The amino acid composition table below shows the correlation between the composition of the purified product and the expected theoretical compositions as deduced from the synthetic gene sequence.

TABLE 5

Amino Acid Analysis of Purified SELP8K

| Amino Acid | pmoles | Actual % composition | Theoretical % composition |
|---|---|---|---|
| Ala | 1623.14 | 12.3 | 12.2 |
| Asx | 122.20 | 0.9 | 0.8 |
| Glx | nd | nd | 0.4 |
| Phe | 58.16 | 0.4 | 0.1 |
| Gly | 5759.31 | 43.7 | 41.5 |
| His | 46.75 | 0.4 | 0.8 |
| Ile | 43.87 | 0.3 | 0 |
| Lys | 198.21 | 1.5 | 1.5 |
| Leu | 39.54 | 0.3 | 0.5 |
| Met | 36.01 | 0.3 | 0.3 |
| Pro | 1534.21 | 11.7 | 12.4 |
| Arg | 70.84 | 0.5 | 0.6 |
| Ser | 703.83 | 5.3 | 6.1 |
| Thr | nd | nd | 0.1 |
| Val | 2797.47 | 21.2 | 22.4 |
| Tyr | 140.87 | 1.1 | 0.1 | nd = none detected

CLP6 Preparation

CLP6 was prepared as described in PCT/US92/09485 using strain pPT0246 (CLP6 referred to as DCP6). The protein polymer was purified in multigram quantities using standard protein purification, extraction, and separation methods. The lyophilized product was a white, spongy material, extremely soluble in water.

```
                                         (SEQ ID NO:16)
CLP6  pPT0246      1,065 AA       MW 85,386
     MDPVVLQRRDWENPGVTQLNRLAAIIP PFASDPM

[(GAHGPAGPK)2 (GAQGPAGPG)24 (GAHGPAGPK)2]4

GAMDPGRYQLSAGRYHYQLVWCCK
```

EXAMPLE 3

The Construction of SELP0K Polymers

Polymer Design Elements

The copolymer structure of SELP8K consists of silk-like blocks (SLP block) and elastin-like blocks (ELP block) in the following sequence: [(SLP block)$_4$ (ELP block)$_8$]. Additional polymers were designed to have different resorption and solution properties by adjusting their silk-like to elastin-like block lengths while maintaining their adhesive properties. SELP0K contains half the length of crystallizable silk-like blocks than SELP8K while maintaining the dispersion frequency with respect to the elastin-like segments.

Polymers with intervening sequences to promote in vivo resorption through proteolytic cleavage by collagenase (92 kd) and cathepsins were also designed. SELP0K is used as the backbone for these designs, but these sites can be used in many different polymer backbone sequences. The insert location is chosen to permit accessibility of the site to the catalytic groove of the protease. Most proteases will bind up to 4 upstream amino acids from the cleavage site. Therefore, the insert sequences should be free of hydrogen bonding and crystallization that may be induced by, for example, silk-like blocks.

The beta structure of the SELP0K will break after the proline of the first elastin-like block. SELP0K-CS1 contains two adjacent cleavage sites for collagenase (PLGP) (SEQ ID NO: 17) within a six amino acid insert. The insertion site was chosen to be removed from the silk-like blocks by at least one proline amino acid (GAGAGS GVGVP L G P L G P GVGVP) (SEQ ID NO: 18). SELP0K-CS2 contains multiple cleavage sites for cathepsins B (ARR), L (FF), S and H (FVR) and plasmin (R) within an eight amino acid insert. The insertion site was chosen to be removed from the silk-like blocks by at least one proline amino acid (GAGAGS GVGVP G F F V R A R R GVGVP)(SEQ ID NO: 19).

Construction of Plasmid pPT0317

Plasmid DNA pSY1262 (see U.S. Pat. No. 5,243,038) was linearized with PvuII REN, then passed through a Probind filter and a Bio-Spin 6 column. The DNA was then treated with Shrimp Alkaline Phosphatase (SAP). The linearized pSY1262 DNA was then ligated with a DNA fragment from pQE-17 (QIAGEN Catalog #33173) prepared as follows. Plasmid DNA pQE-17 was digested with BglII and HindIII RENs and the 36 bp fragment shown in Table 6 was purified using a Probind filter and a Biospin column. The DNA was purified further using a Microcon-30 filter and the filtrate, containing the 36 bp fragment, was kept. The DNA was then treated with DNA Polymerase I and purified using a Probind filter and a Biospin column (see Example 1).

TABLE 6

```
5'-GATCTTCGATCTCATCACCATCACCATCACTA  (SEQ ID NO:20)

3'-AAGCTAGAGTAGTGGTAGTGGTAGTGATTCGT  (SEQ ID NO:21)
```

The product of the ligation reaction was transformed into *E. coli* strain HB101. Plasmid DNA from transformants was purified and analyzed by digestion using Bst1107I and EcoRV RENs. The clones containing the desired DNA fragment were further digested with Bst1107I and BstYI RENs to determine the orientation of the insert. Plasmid DNA from the clones showing the correct restriction pattern was purified and analyzed by DNA sequencing. Plasmid pPT0317 contained the desired DNA insert and was used for further DNA constructions.

SELP0K Polymer Construction

One oligonucleotide strand as shown in Table 7 was synthesized using an Applied Biosystems DNA synthesizer model 381A and a 2000 Å synthesis column supplied by Glen Research. After the synthesis the 93 base DNA fragment was deprotected and cleaved from the column support by treatment in ammonium hydroxide at 55° C. for 6 hours.

TABLE 7

(SEQ ID NO:22)
```
5'-
ATGGCAGCGAAAGGGGACCGGTGCCGGCGCAGGTAGCGGAGCCGGTGCGG
GCTCAAAAAGGGCTCTGGTGCCTTTCCGCTAAAGTCCTGCCGT-3'
```

The PCR reaction was performed using the same two DNA primer strands as described for the construction of the SELP8K gene monomer and the reaction product was purified. The DNA was resuspended and digested with BanI REN. The digested DNA was then separated by low-melting agarose gel and ligated with pPT0285 (see PCT/US92/09485) previously digested with BanI REN and purified by NACS column. The product of the ligation reaction was transformed into E. coli strain HB101. Plasmid DNA from transformants was purified and analyzed by digestion using EcoRI and BanII RENs. Plasmid DNA from the clones showing the correct restriction pattern was then purified and analyzed by DNA sequencing. Plasmid pPT0358 contained the desired sequence and was used for subsequent DNA constructions.

Plasmid DNA from pPT0340 was digested with BanII REN and the digestion fragments were separated by agarose gel electrophoresis. The SELP0K gene fragment, 156 bp, (see Table 8), was excised and purified using an Ultrafree-MC filter followed by Bio-Spin 6 column.

TABLE 8

(SEQ ID NOS:23&24)
```
BanII
G GGC TCT GGT GTT GGA GTG CCA GGT GTC GGT GTT CCG
C CCG AGA CCA CAA CCT CAC GGT CCA CAG CCA CAA GGC
  G   S   G   V   G   V   P   G   V   G   V   P

GGT GTA GGC GTT CCG GGA GTT GGT GTA CCT GGA AAA
CCA CAT CCG CAA GGC CCT CAA CCA CAT GGA CCT TTT
 G   V   G   V   P   G   V   G   V   P   G   K

GGT GTT CCG GGG GTA GGT GTG CCG GGC GTT GGA GTA
CCA CAA GGC CCC CAT CCA CAC GGC CCG CAA CCT CAT
 G   V   P   G   V   G   V   P   G   V   G   V

CCA GGT GTA GGC GTC CCG GGA GCG GGT GCT GGT AGC
GGT CCA CAT CCG CAG GGC CCT CGC CCA CGA CCA TCG
 P   G   V   G   V   P   G   A   G   A   G   S
```

TABLE 8-continued
```
        BanII
GGC GCA GGC GCG GGC TC
CCG CGT CCG CGC CCG AG
 G   A   G   A   G   S
```

The purified fragment was ligated with plasmid pPT0358 which had been digested with BanII REN, then passed through a Probind filter and a Microcon-30 filter. The digestion fragments were then separated by agarose gel electrophoresis. The plasmid DNA was then excised and purified using an Ultrafree-MC filter followed by Bio-Spin 6 column (see Example 1).

The product of this ligation reaction was transformed into E. coli strain HB101. Transformants were selected for resistance to chloramphenicol. Plasmid DNA from individual transformants was purified and analyzed for increased size due to SELP0K multiple DNA insertion. Several clones were obtained with inserts of different sizes. Plasmid pPT0359, pPT0360 and pPT0374 containing respectively 18, 2 and 6 repeats of the SELP0K gene monomer were used for subsequent constructions.

Plasmid DNA from pPT0359 and pPT0374 was digested with BanI REN and the digestion fragments were separated by agarose gel electrophoresis. The SELP0K gene fragments, approximately 2800 bp and 1000 bp, were excised and purified by NACS column. The purified fragments were then ligated with plasmid pPT0317 which had been digested with BanI REN, then passed through a Probind filter and a Bio-Spin 6 column. The DNA was then treated with Shrimp Alkaline Phosphatase (SAP), passed through a Probind filter and then a Bio-Spin 6 column (see Example 1).

The product of these ligation reactions was transformed into E. coli strain HB101. Transformants were selected for resistance to kanamycin. Plasmid DNA from individual transformants was purified and analyzed for increased size due to SELP0K multiple DNA insertion. Several clones were obtained. Plasmid pPT0364 and pPT0375 were chosen to be used for expression of SELP0K.

SELP0K Expression Analysis

E. coli strain HB101 containing plasmid pPT0364 and pPT0375 were grown as described in Example 1. The proteins produced by these cells were analysed by SDS-PAGE for detection of reactivity to ELP antibodies. In every analysis a strong reactive band was observed of an apparent molecular weight of approximately 95 kD and 35 kD respectively.

pPT0364    SELPOK    1000 AA    MW 80,684

MDPVVLQRRDWENPGVTQLNRLAAHPPFASDPM          (SEQ ID NO:25)

[(GAGAGS)$_2$ (GVGVP)$_4$ GKGVP (GVGVP)$_3$]$_{18}$ (GAGAGS)$_2$ GAGAMDPGRYQDLRSHHHHHH pPT0375    SELPOK    376 AA    MW 31,445

MDPVVLQRRDWENPGVTQLNRLAAHPPFASDPM          (SEQ ID NO:26)

[(GAGAGS)$_2$ (GVGVP)$_4$ GKGVP (GVGVP)$_3$]$_6$ (GAGAGS)$_2$ GAGAMDPGRYQDLRSHHHHHH

SELP0K-CS1 Polymer Construction

Plasmid pPT0360 was digested with BanI REN and the digestion fragments were separated by agarose gel electrophoresis. The SELP0K gene fragment, approximately 300 bp, was excised and purified using an Ultrafree-MC filter followed by Bio-Spin 6 column. The purified fragment was ligated with plasmid pPT0134 (see PCT/US92/09485) which had been digested with FokI REN. The enzyme was heat inactivated at 65° C. for 20 minutes and the ligation mixture was then passed through a Probind filter. The DNA was then treated with Shrimp Alkaline Phosphatase (SAP), passed through a Probind filter and then a Bio-Spin 6 column.

The product of this ligation reaction was transformed into E. coli strain HB101. Transformants were selected for resistance to chloramphenicol. Plasmid DNA from individual transformants was purified and analyzed by digestion using DraI REN. One plasmid, pPT0363, showed the correct restriction pattern and was used for subsequent DNA constructions.

One oligonucleotide strand as shown in Table 9 was synthesized using an Applied Biosystems DNA synthesizer model 381A and a 2000 Å synthesis column supplied by Glen Research. After the synthesis the 141 base DNA fragment was deprotected and cleaved from the column support by treatment in ammonium hydroxide at 55° C. for 6 hours.

TABLE 9

(SEQ ID NO:27)
5'-ATGGCAGCGAAAGGGGACCGCCGGTGCGGGCTCTGGTGTTGGAGTGC

CGCTGGGTCCTCTTGGCCCAGGTGTCGGTGTTCCGGGTGTAGGCGTTCCG

GGAGTTGGTGTACCTGGAAAAGGTTTCCGCTAAGTCCTGCCGT-3'

The PCR reaction was performed using the same two DNA primer strands as described for the construction of the SELP8K gene monomer and the reaction product was purified. The DNA was then resuspended and digested with BsrFI and EcoNI RENs. The digested DNA was treated with Probind and Microcon-30 filters, a Bio-Spin 6 column, and then ligated with pPT0363 previously digested with BsrFI REN, treated with a ProBind filter and a Bio-Spin 6 column and then further digested with EcoNI REN. The digestion fragments were separated by agarose gel electrophoresis. The larger DNA band, approximately 2000 bp, was excised and purified using an Ultrafree-MC filter followed by Bio-Spin 6 column (see Example 1).

The product of the ligation reaction was transformed into E. coli strain HB101. Plasmid DNA from individual transformants was purified and analyzed by digestion using Asp700I and EcoO109I RENs. Plasmid DNA from the clones showing the correct restriction pattern was then purified and analyzed by DNA sequencing. Plasmid pPT0368 (see Table 10) contained the desired sequence and was used for subsequent DNA constructions.

TABLE 10

(SEQ ID NOS:28 & 29)
```
BanII
G GGC TCT GGT GTT GGA GTG CCG CTG GGT CCT CTT GGC
C CCG AGA CCA CAA CCT CAC GGC GAC CCA GGA GAA CCG
    G   S   G   V   G   V   P   L   G   P   L   G
```

TABLE 10-continued

```
CCA GGT GTC GGT GTT CCG GGT GTA GGC GTT CCG GGA
GGT CCA CAG CCA CAA GGC CCA CAT CCG CAA GGC CCT
 P   G   V   G   V   P   G   V   G   V   P   G

GTT GGT GTA CCT GGA AAA GGT GTT CCG GGG GTA GGT
CAA CCA CAT GGA CCT TTT CCA CAA GGC CCC CAT CCA
 V   G   V   P   G   K   G   V   P   G   V   G

GTG CCG GGC GTT GGA GTA CCA GGT GTA GGC GTC CCG
CAC GGC CCG CAA CCT CAT GGT CCA CAT CCG CAG GGC
 V   P   G   V   G   V   P   G   V   G   V   P

BanII
GGA GCG GGT GCT GGT AGC GGC GCA GGC GCG GGC TCT
CCT CGC CCA CGA CCA TCG CCG CGT CCG CGC CCG AGA
 G   A   G   A   G   S   G   A   G   A   G   S
```

Plasmid DNA pPT0368 was digested with BanII REN, and the digestion fragments were separeted by agarose gel electrophoresis. The SELP0K-CS1 gene fragment, 174 bp, was excised and purified using an Ultrafree-MC filter followed by Bio-Spin 6 column. The purified fragment was ligated with plasmid pPT0358 which had been digested with BanII REN, then passed through a Probind filter and a Microcon-30 filter. Subsequently the digestion fragments were separated by agarose gel electrophoresis. The plasmid DNA was then excised and purified using an Ultrafree-MC filter followed by Bio-Spin 6 column (see Example 1).

The product of this ligation reaction was transformed into E. coli strain HB101. Transformants were selected for resistance to chloramphenicol. Plasmid DNA from individual transformants was purified and analyzed for increased size due to SELP0K-CS1 multiple DNA insertion. Several clones were obtained with insert sizes ranging from 1000 bp to approximately 3000 bp. Plasmid pPT0369 containing 16 repeats of the SELP0K-CS1 gene monomer was used for subsequent constructions.

Plasmid DNA from pPT0369 was digested with BanI REN, followed by a Probind filter and then the digestion fragments were separated by agarose gel electrophoresis. The SELP0K-CS1 gene fragment, approximately 2800 bp, was excised and purified by an Ultrafree-MC filter and desalted using a Bio-Spin 6 column. The purified fragments were then ligated with plasmid pPT0317 which had been digested with BanI REN and then passed through a Probind filter and a Bio-Spin 6 column. The DNA was then treated with Shrimp Alkaline Phosphatase (SAP), passed through a Probind filter and then a Bio-Spin 6 column (see Example 1).

The product of these ligation reactions was transformed into E. coli strain HB101. Transformants were selected for resistance to kanamycin. Plasmid DNA from individual transformants was purified and analyzed for increased size due to SELP0K-CS1 multiple DNA insertion. Several clones were obtained. Plasmid pPT0370 was chosen to be used for expression of SELP0K-CS1.

SELP0K-CS1 Expression Analysis

E. coli strain HB101 containing plasmid pPT0370 was grown as described in Example 1. The proteins produced by these cells were analysed by SDS-PAGE for detection of reactivity to ELP antibodies. In every analysis a strong reactive band was observed with an apparent molecular weight of approximately 90 kD.

```
pPT0370      SELPOK-CS1      934 AA       (SEQ ID NO:30)
76,389                                    MW
     MDPVVLQRRDWENPGVTQLNRLAAHPPFASDPM
        [(GAGAGS)₂ (GVGVP)₁ LGPLGP (GVGVP)₃ GKGVP (GVGVP)₃]₁₅
        (GAGAGS)₂ GAGAMDPGRYQDLRSHHHHHH
```

SELP0K-CS2 Polymer Construction

One oligonucleotide strand as shown in Table 11 was synthesized using an Applied Biosystems DNA synthesizer model 381A and a 2000 Å synthesis column supplied by Glen Research. After the synthesis the 147 base DNA fragment was deprotected and cleaved from the column support by treatment in ammonium hydroxide at 55° C. for 6 hours.

TABLE 11

(SEQ ID NO:31)
5'-ATGGCAGCGAAAGGGGACCGCCGGTGCGGGCTCTGGTGTTGGAGTGC

CAGGCTTCTTTGTACGTGCACGCCGTGGTGTCGGTGTTCCGGGTGTAGGC

GTTCCGGGAGTTGGTGTACCTGGAAAAGGTTTCCGCTAAAGTCCTGCCG

T-3'

The PCR reaction was performed using the same two DNA primer strands as described for the construction of the SELP8K gene monomer and the reaction product was purified. The DNA was then resuspended and digested with BsrFI and EcoNI RENs. The digested DNA was treated with ProBind and Microcon-30 filters, a Bio-Spin 6 column, and then ligated with pPT0363 previously digested with BsrFI REN, treated with a ProBind filter and a Bio-Spin 6 column and then further digested with EcoNI REN. The digestion fragments were separated by agarose gel electrophoresis. The larger DNA band, approximately 2000 bp, was excised and purified using an Ultrafree-MC filter followed by Bio-Spin 6 column.

The product of the ligation reaction was transformed into E. coli strain HB101. Plasmid DNA from individual transformants was purified and analyzed by digestion using Asp700I and DraIII RENs. Plasmid DNA from the clones showing the correct restriction pattern was then purified and analyzed by DNA sequencing. Plasmid pPT0367 (see Table 12) contained the desired sequence and was used for subsequent DNA constructions.

TABLE 12

(SEQ ID NOS:32 & 33)
```
BanII
G GGC TCT GGT GTT GGA GTG CCA GGC TTC TTT GTA CGT
C CCG AGA CCA CAA CCT CAC GGT CCG AAG AAA CAT GCA
    G   S   G   V   G   V   P   G   F   F   V   R

GCA CGC CGT GGT GTC GGT GTT CCG GGT GTA GGC GTT
CGT GCG GCA CCA CAG CCA CAA GGC CCA CAT CCG CAA
 A   R   G   V   G   V   P   G   V   G   V

CCG GGA GTT GGT GTA CCT GGA AAA GGT GTT CCG GGG
GGC CCT CAA CCA CAT GGA CCT TTT CCA CAA GGC CCC
 P   G   V   G   V   P   G   K   G   V   P   G

GTA GGT GTG CCG GGC GTT GGA GTA CCA GGT GTA GGC
CAT CCA CAC GGC CCG CAA CCT CAT GGT CCA CAT CCG
 V   G   V   P   G   V   G   V   P   G   V   G

GTC CCG GGA GCG GGT GCT GGT AGC GGC GCA GGC GCG
CAG GGC CCT CGC CCA CGA CCA TCG CCG CGT CCG CGC
 V   P   G   A   G   A   G   S   G   A   G   A

BanII
  GGC TC
  CCG AG
  G   S
```

Plasmid DNA pPT0367 was digested with BanII REN, treated with a Probind filter and a Bio-Spin6 column and then the digestion fragments were separated by agarose gel electrophoresis. The SELP0K-CS2 gene fragment, 180 bp, was excised and purified using an Ultrafree-MC filter followed by Bio-Spin 6 column. The purified fragment was ligated with plasmid pPT0358 which had been digested with BanII REN and then passed through a Probind filter and a Microcon-30 filter. Subsequently the digestion fragments were separated by agarose gel electrophoresis. The plasmid DNA was then excised and purified using an Ultrafree-MC filter followed by Bio-Spin 6 column (see Example 1).

The product of this ligation reaction was transformed into E. coli strain HB101. Transformants were selected for resistance to chloramphenicol. Plasmid DNA from individual transformants was purified and analyzed for increased size due to SELP0K-CS2 multiple DNA insertion. Several clones were obtained with insert sizes ranging from 200 bp to approximately 3000 bp. Plasmid pPT0371 and pPT0372, containing 18 and 15 repeats respectively of the SELP0K-CS2 gene monomer were used for subsequent constructions.

Plasmid DNA from pPT0372 was digested with BanI REN, followed by a Probind filter, and then the digestion fragments were separated by agarose gel electrophoresis. The SELP0K-CS2 gene fragment, approximately 2800 bp, was excised and purified by an Ultrafree-MC filter and desalted using a Bio-Spin 6 column. The purified fragments were then ligated with plasmid pPT0317 which had been digested with BanI REN, passed through a Probind filter and then a Bio-Spin 6 column. The DNA was treated with Shrimp Alkaline Phosphatase (SAP), passed through a Probind filter and then a Bio-Spin 6 column (see Example 1).

The product of these ligation reactions was transformed into E. coli strain HB101. Transformants were selected for resistance to kanamycin. Plasmid DNA from individual transformants was purified and analyzed for increased size due to SELP0K-CS2 multiple DNA insertion. Several clones were obtained. Plasmid pPT0373 was chosen to be used for the expression of SELP0K-CS2.

SELP0K-CS2 Expression Analysis

E. coli strain HB101 containing plasmid pPT0373 was grown as described in Example 1. The proteins produced by these cells were analysed by SDS-PAGE for detection of reactivity to ELP antibodies. In every analysis a strong reactive band was observed of an apparent molecular weight of approximately 90 kD.

pPT0373   SELP0K-CS2        964 AA    (SEQ ID NO:34)
                                      MW 83,218
MDPVVLQRRDWENPGVTQLNRLAAHPPFASDPM
[(GAGAGS)₂ (GVGVP)₁ GFFVRARR (GVGVP)₃ GKGVP
(GVGVP)₃]₁₅ (GAGAGS)₂ GAGAMDPGRYQDLRSHHHHHH

SELP0K and SELP0K-CS1 Purification

SELP0K and SELP0K-CS1 were produced in *E. coli* strains pPT0364 and pPT0370, respectively. The products were purified from the cellular biomass by means of cellular lysis, clearance of insoluble debris by polyethylene imine precipitation and centrifugation, ammonium sulfate precipitation, and anion exchange chromatography. The purified products were analyzed by sodium dodecyl sulfate polyacrylamide gel electrophoresis (SDS-PAGE), immunoreactivity with a polyclonal antisera which reacts with elastin-like peptide blocks (ELP antibody), and amino acid analysis.

For SELP0K, a protein band of apparent molecular weight 95,000 was observed by amido black staining of SDS-PAGE separated and transferred samples and the same band reacted with the ELP antibody on Western blots. As expected, amino acid analysis (shown in Table 13) indicated that the product was enriched for the amino acids glycine (41.0%), alanine (8.0%), serine (4.5%), proline (14.1%), and valine (26.8%). The product also contained 1.9% lysine. The amino acid composition table below shows the correlation between the composition of the purified product and the expected theoretical composition as deduced from the synthetic gene sequence.

TABLE 13

Amino Acid Analysis of Purified SELP0K

|   | pMoles | Mole % | Theoretical Mole % |
|---|---|---|---|
| ASX | 28.10 | 0.6 | 0.7 |
| GLX | 26.90 | 0.6 | 0.4 |
| SER | 199.84 | 4.5 | 4.0 |
| GLY | 1812.07 | 41.0 | 40.5 |
| HIS | 28.45 | 0.6 | 0.7 |
| ARG | 20.49 | 0.5 | 0.5 |
| THR | 0 | 0.0 | 0.1 |
| ALA | 355.29 | 8.0 | 8.0 |
| PRO | 623.22 | 14.1 | 15.0 |
| TYR | 8.47 | 0.2 | 0.1 |
| VAL | 1183.63 | 26.8 | 27.3 |
| MET | 17.21 | 0.4 | 0.3 |
| ILE | 4.83 | 0.1 | 0.0 |
| LEU | 20.66 | 0.5 | 0.4 |
| PHE | 7.57 | 0.2 | 0.1 |
| LYS | 84.02 | 1.9 | 1.8 |
| Total | 4420.75 | | |

For SELP0K-CS1, a protein band of apparent molecular weight 90,000 was observed by amido black staining of SDS-PAGE separated and transferred samples and the same band reacted with the ELP antibody on Western blots. As expected, amino acid analysis (shown in Table 14) indicated that the product was enriched for the amino acids glycine (40.0%), alanine (7.6%), serine (5.2%), proline (16.3%), and valine (23.3%). The product also contained 1.5% lysine. The amino acid composition table below shows the correlation between the composition of the purified product and the expected theoretical composition as deduced from the synthetic gene sequence.

TABLE 14

Amino Acid Analysis of Purified SELP0K-CS1

|   | pMoles | Mole % | Theoretical Mole % |
|---|---|---|---|
| ASX | 16.43 | 0.7 | 0.7 |
| GLX | 10.59 | 0.5 | 0.4 |
| SER | 119.96 | 5.2 | 3.6 |
| GLY | 924.51 | 40.0 | 39.6 |
| HIS | 13.85 | 0.6 | 0.7 |
| ARG | 11.26 | 0.5 | 0.5 |
| THR | 0 | 0.0 | 0.1 |
| ALA | 175.07 | 7.6 | 7.3 |
| PRO | 376.40 | 16.3 | 16.7 |
| TYR | 2.49 | 0.1 | 0.1 |
| VAL | 537.96 | 23.3 | 24.5 |
| MET | 5.19 | 0.2 | 0.3 |
| ILE | 0 | 0.0 | 0.0 |
| LEU | 76.62 | 3.3 | 0.4 |
| PHE | 2.58 | 0.1 | 0.1 |
| LYS | 35.68 | 1.5 | 1.6 |
| Total | 2308.59 | | |

EXAMPLE 4

Evaluation of CLP6 and SELP8K Properties

Test Procedures

Tiseel Adhesive Systems.

Rat skins were washed with water, blotted dry and cut into strips about 1 cm×4 cm. Adhesive from Tiseel Kit VH (Osterreiches Institute Fur Haemoderivate, GmbH, A-1220, Vienna, Austria) was applied according to the manufacturer's specifications.

Rat Skin Lap Shear Tensile Strength Assay.

Adhesive formulations were tested for their ability to bond skin together using an in vitro rat skin lap shear tensile strength assay. Adhesives were applied to the subcutaneous side of a strip of harvested rat skin. A second skin strip was overlapped in order to produce an approximate bonding surface of 1 cm². A 100 gram weight was applied to the lap joint and the adhesive was allowed to cure, usually at room temperature for a period of 2 hours and wrapped in plastic to prevent desiccation. The lap joint was mounted on an Instron Tensile Tester or similar apparatus and tensile force applied. With the Instron, tensile force was typically applied at a constant strain rate of 2 inches per minute. The load at failure was recorded and normalized to the measured area of overlap.

Adhesive Systems with Glutaraldehyde.

Rat skins were washed with water, blotted dry, and cut into strips about 1 cm×4 cm. Glutaraldehyde was distilled, stored frozen and thawed immediately before use. Bovine serum albumin was dissolved according to Goldman's specifications (Goldman, WO94/01508). CLP6 was dissolved at 600 mg/mL in 150 mM HEPES+30 mM NaCl and adjusted to pH 7.5. SELP8K was dissolved at the concentrations indicated in Table 15 in 150 mM HEPES+45 mM NaCl and adjusted to pH 8. The indicated aliquots of the solution of protein was spread over both skins before the addition of the glutaraldehyde solution. The second skin was overlaid, rubbed across the lower skin to distribute the components, adjusted to an overlap area of ca. 1 cm², covered with plastic wrap to prevent drying, and cured for 2 hours at 25° C. under a compressive force of 100 g/cm².

Adhesive Systems with 1,6-(Diisocyanto)hexane.

Rat skins were washed with water, blotted dry, and cut into strips about 1 cm×4 cm. A solution of SELP8K was made up in the specified buffer at a concentration of ca. 50% w/w. A 1:1 v/v mixture of hexamethylene diisocyanate (HMDI) and Pluronic L-61 surfactant was prepared. A 20 µL aliquot of SELP8K solution was applied to one skin followed by a 2 µL aliquot of the diluted HMDI. The second skin was overlaid, rubbed across the lower skin to mix the components, adjusted to ca. 1 cm² overlap, covered with plastic wrap to prevent drying, and cured for 2 hours at 25° C. under a compressive force of 100 g/cm².

Results

In order to provide a baseline for subsequent adhesive experiments, ethyl cyanoacrylate and Tiseel fibrin glue were evaluated. These results are reported in the following table.

TABLE 15

Base Case Lap Shear Tensile Strengths

| Reagent | Dose | Tensile Strength g/cm² |
|---|---|---|
| Normal Saline | not applicable | 13 ± 4 |
| Tiseel Fibrin Glue | ~25 mg | 261 ± 51 |
| Ethyl cyanoacrylate | 25 mg | 385 ± 119 |

All data reported are based on at least three test specimens. All test results are based on a two hour cure time.

The subject compositions were compared to the proteinaceous adhesive system described by Goldman (WO94/01508). Ten microliters of glutaraldehyde solution of the indicated concentration was added in all cases. The following table indicates the results.

TABLE 16

Lap Shear Tensile Strength of Glutaraldehyde Cured Adhesive Systems

| Reagent | | Dose | Tensile Strength g/cm² |
|---|---|---|---|
| Ovalbumin (30 µ) 200 mg/mL | + Glutaraldehyde 10 µL 2.5 N | 6 mg/2.5 mg | 50 ± 10 |
| Atelocollagen (denat) (25 µL) 125 mg/mL | + Glutaraldehyde 10 µL 2.5 N | 3 mg/2.5 mg | 148 ± 47 |
| CLP6 (40 µL) 600 mg/mL | + Glutaraldehyde 10 µL 2.5 N | 24 mg/2.5 mg | 306 ± 98 |
| CLP6 (20 µL) 600 mg/mL | + Glutaraldehyde 10 µL 2.5 N | 12 mg/2.5 mg | 171 ± 42 |
| SELP8K (30 µL) | + Glutaraldehyde | 18 mg/1 mg | 545 ± 153 |
| 600 mg/mL | 1.0 N | 9 mg/1 mg | 452 ± 54 |
| 300 mg/mL | 1.0 N | 9 mg/1 mg | 234 ± 51* |
| 300 mg/mL (impure) | 1.0 N | 9 mg/0.1 mg | 210 ± 57* |
| 300 mg/mL (impure) | 0.1 N | 7 mg/2.5 mg | 374 ± 90 |
| 287 mg/mL | 2.5 N | 3 mg/1 mg | 361 ± 47 |
| 100 mg/mL | 1.0 N | 3 mg/2.5 mg | 274 ± 17 |
| 100 mg/mL | 2.5 N | | |

*This preparation of SELP8K was known to be impure and is estimated to yield adhesive strength about one-half of that of the more completely purified material.

The data in the above table demonstrate that the subject polymers are able to provide superior adhesive capabilities when used in the glutaraldehyde cured system under conditions comparable to collagen and ovalbumin. Despite the lower number of amino groups available for crosslinking, the SELP8K polymer provides the highest tensile strengths in the rat skin lap shear results. The above results demonstrate that significant adhesion can be obtained at even low doses of glutaraldehyde down to 100 µg/cm². The quality and purity of the glutaraldehyde is known to be critical to obtain good crosslinking (Rujigrok, DeWijn, Boon, *J. Matr. Sci. Matr. Med.* 5:80-87 (1994); Whipple, Ruta, *J. Org. Chem.* 39:1666-1668 (1974). The glutaraldehyde used in these experiments was distilled, diluted to 2.5N and stored at −20° C. until used.

In the next study, hexamethylene diisocyanate was employed. It was found necessary to add an equal volume of diluent to obtain good adhesion, since the curing was otherwise too fast. The following table indicates the results, where n=12.

TABLE 17

Lap Shear Tensile Strength of HMDI Derived Adhesive System

| Reagent | | Dose | Tensile Strength g/cm² |
|---|---|---|---|
| SELP8K | 20 µL × 50% w/w | 10 mg | 585 + 203 |
| HMDI/L-61 1:1 v/v | 2 µL × 50% v/v | 1 mg | |
| Buffer: (100 µL water + 10 µL 1M KHCO₃) | | | |
| SELP8K | 20 µL × 50% w/w | 10 mg | 503 ± 21 |
| HMDI/L-61 1:1 v/v | 2 µL × 50% v/v | 1 mg | |
| Buffer: (100 µL 50 mM PO₄ (pH 6.8) + 5 µL 1 M KHCO₃) | | | |
| SELP8K | 20 µL × 50% w/w | 10 mg | 451 ± 67 |
| HMDI/L-61 1:1 v/v | 2 µL × 50% v/v | 1 mg | |
| Buffer: (100 µL 50 mM PO₄ (pH 6.8) + 10 µL 1M KHCO₃) | | | |
| SELP8K | 2 µL × 50% w/w | 10 mg | 362 ± 71 |
| HMDI/L-61 1:1 v/v | 2 µL × 50% v/v | 1 mg | |
| Buffer: (100 µL 50 mM PO₄ (pH 6.8)) | | | |

EXAMPLE 5

Evaluation of SELP0K (SE0K) AND SELP0K-CS1 Properties

A number of formulations were prepared using different components for the formulation and determining the lap shear strength. In addition a variety of protocols were used to prepare the protein dope to provide adhesion. These protocols are set forth as follows:

| Protocol A. | |
|---|---|
| SE0K | 17% w/w |
| Lysine hydrochloride | 1:2 |
| Potassium carbonate | 1:1 |
| Isocyanate:Amine | 13.1:1 |

Preparation of Protein Dope

The designation 1:2 refers to the nominal ratio of amino groups derived from lysine to amino groups derived from SE0K. The designation 1:1 refers to the nominal ratio of carbonate ions per amino group from SE0K plus lysine. The designation 13.1:1 refers to the nominal ratio of isocyanate groups to amine groups from SE0K plus lysine.

A stock buffer solution was prepared by dissolving lysine hydrochloride 0.0157 g, potassium carbonate 0.0710 g, and Evans Blue dye 0.00371 g in 7.526 mL of deionized water. Stock buffer, 620.6 μL, was added to SE0K, 127.1 mg in an Eppendorf tube. The mixture was agitated on a vortex mixer until complete dissolution occurred. The solution was centrifuged at about 5000 rpm for 30-60 seconds to separate air bubbles. The solution was then loaded into a 1 mL syringe for dispensing onto the test skins. The optional inclusion of dye in the protein dope serves to more readily visualize the distribution of the dope on the test skins.

Preparation of HMDI Setting Agent

The HMDI setting agent was prepared by dissolving Sudan Red dye, 1.75 mg, in neat 1,6-diisocyanatohexane, 1.00 g. The optional inclusion of dye in the setting agent serves to more readily visualize the distribution of the setting agent on the test skins.

Preparation of Rat Skins

Freshly harvested rat hides were stored frozen at −20° C. Just before use the hides were thawed and cut into 1 cm×3 cm strips. All fascia was removed from the strips of skin with a razor blade. Strips of skin were selected which were uniform in width and thickness. Prepared rat skin samples were temporarily stored at 37° C. between gauze pads soaked with PBS and contained in a plastic bag to prevent drying.

Application of Adhesive

In a 37° C. warm room, protein dope, 15 μL, was applied to each of two strips of rat skin, 30 μL total, and aggressively worked into about a 1 cm² area of each piece of skin with a stainless steel spatula. A total of 1.8 μL of HMDI setting agent was applied to the skins, apportioned so that 3 parallel stripes of HMDI were applied to the first skin and two stripes in an X-pattern were applied to the second skin. The skins were immediately assembled to form the lap joint, covered with a piece of plastic film to prevent drying, and compressed under a 100 g weight. The joint was allowed to cure for 15 minutes at 37° C. The length and width of the lap joint was measured to 1 mm using a ruler immediately before tensile testing on an Instron Model 55 test machine. The crosshead speed was set at 25 mm per minute. Lap shear tensile strengths were reported in units of g/cm². Means and standard deviations were calculated for measurements conducted at least in triplicate.

| Protocol B. | |
|---|---|
| SE0K | 17% w/w |
| Lysine hydrochloride | 1:2 |
| Potassium carbonate | 1:1 |
| Isocyanate:Amine | 14.5:1 |

The steps of Protocol A were followed, except that bubbles were removed from the protein dope in a two stage process. After centrifugation, the dope was exposed to reduced pressure, 26 in-Hg, for 30 minutes. The volume of HMDI setting agent applied to the lap joint was 2.0 μL.

| Protocol C. | |
|---|---|
| SE0K | 17% w/w |
| Lysine hydrochloride | 1:2 |
| Potassium carbonate | 1:1 |
| Isocyanate:Amine | 7.3:1 |

The steps of Protocol B were followed, except that the composition of the HMDI setting agent was altered. Sudan Red dye, 5.2 mg was dissolved in 10.735 g of neat Pluronic surfactant L-31 by heating to 100° C. for 10 minutes. After cooling to room temperature, an equal weight of 1,6-diisocyanatohexane was added to this mixture. The mixture was prepared immediately before use.

| Protocol D1. | |
|---|---|
| SE0K | 17% w/w |
| Lysine hydrochloride | 1:2 |
| Potassium carbonate | 1:1 |
| Isocyanate:Amine | 14.5:1 |

The steps of Protocol B were followed, except that Pluronic surfactant L-31, 4.57 mg, was added to SE0K, 74.6 mg. The ratio of SE0K to lysine buffer solution remained as described in Protocol B.

| Protocol D2. | SE0K | 17% w/w |
|---|---|---|
| | Lysine hydrochloride | 1:2 |
| | Potassium carbonate | 1:1 |
| | Isocyanate:Amine | 14.5:1 |

The steps of Protocol B were followed, except that Pluronic surfactant L-31, 1.07 mg, was added to SE0K, 74.7 mg. The ratio of SE0K to lysine buffer solution remained as described in Protocol B.

| Protocol E. | SE0K | 17% w/w |
|---|---|---|
| | Lysine hydrochloride | 1:2 |
| | Potassium carbonate | 1:1 |
| | Isocyanate:Amine | 7.3:1 |

The steps of Protocol B were followed, except that in Protocol E, 5.1 mg Pluronic L-31 was added to 85.0 mg SE0K. The composition of the HMDI setting agent was also altered. Sudan Red dye, 5.2 mg was dissolved in 10.735 g neat Pluronic surfactant L-31 by heating to 100° C. for 10 minutes. After cooling to room temperature, an equal weight of 1,6-diisocyanatohexane was added to this mixture. The mixture was prepared immediately before use.

| Protocol F. | SE0K | 17% w/w |
|---|---|---|
| | Lysine hydrochloride | 1:2 |
| | Sodium Borate | pH 9.5 |
| | Isocyanate:Amine | 14.5:1 |

The steps of Protocol B were followed, except that a stock buffer solution was prepared by dissolving lysine hydrochloride 0.46 g, boric acid 1.24 g in 92.2 mL of deionized water. The pH of this solution was adjusted to pH 9.52 by the addition of 7.8 mL of 2 N sodium hydroxide solution. Evans Blue dye, 0.50 mg/mL, was dissolved in this buffer, and the solution filtered through a 0.45 micron syringe filter. Stock buffer, 333.5 μL, was added to SE0K, 68.3 mg in an Eppendorf tube. The mixture was agitated on a vortex mixer until complete dissolution occurred.

| Protocol G. | SE0K | 17% w/w |
| --- | --- | --- |
| | Lysine hydrochloride | 1:2 |
| | Potassium Borate | pH 9.5 |
| | Isocyanate:Amine | 14.5:1 |

The steps of Protocol B were followed, except that a stock buffer solution was prepared by dissolving lysine hydrochloride, 0.46 g, and boric acid, 1.24 g in 99.1 mL of deionized water. The pH of this solution was adjusted to pH 9.52 by the addition of 0.9 mL of 10 N potassium hydroxide solution. Evans Blue dye, 0.50 mg/mL, was dissolved in this buffer, and the solution filtered through a 0.45 micron syringe filter. Stock buffer, 367.2 µL, was added to SE0K, 75.2 mg in an Eppendorf tube. The mixture was agitated on a vortex mixer until complete dissolution occurred.

| Protocol H. | SE0K | 17% w/w |
| --- | --- | --- |
| | Lysine hydrochloride | 1:2 |
| | Lithium Carbonate | pH 9.5 |
| | Isocyanate:Amine | 14.5:1 |

The steps of Protocol B were followed, except that the stock buffer solution was prepared by dissolving lysine hydrochloride, 42.7 mg, in deionized water, 10.0 mL, and adding lithium carbonate, 14.3 mg, to pH 9.55. Evans Blue dye, 0.50 mg/mL, was dissolved in this buffer, and the solution filtered through a 0.45 micron syringe filter.

| Protocol I. | SE0K | 17% w/w |
| --- | --- | --- |
| | Lysine hydrochloride | 1:2 |
| | Sodium Carbonate | pH 9.5 |
| | Isocyanate:Amine | 14.5:1 |

The steps of Protocol B were followed, except that the stock buffer solution was prepared by dissolving sodium carbonate, 1.06 g, and lysine hydrochloride, 0.46 g, in 99.2 mL of deionized water. Using concentrated hydrochloric acid solution 0.8 mL, the solution was adjusted to pH 9.54. Evans Blue dye, 0.50 mg/mL, was dissolved in this buffer, and the solution filtered through a 0.45 micron syringe filter.

| Protocol J. | SE0K | 17% w/w |
| --- | --- | --- |
| | Lysine hydrochloride | 1:2 |
| | Potassium Carbonate | pH 9.5 |
| | Isocyanate:Amine | 14.5:1 |

The steps of Protocol B were followed, except that the stock buffer solution was prepared by dissolving potassium carbonate, 1.38 g, and lysine hydrochloride, 0.46 g, in 99.1 mL of deionized water. Using concentrated hydrochloric acid solution, 0.9 mL, the solution was adjusted to pH 9.53. Evans Blue dye, 0.50 mg/mL, was dissolved in this buffer, and the solution filtered through a 0.45 micron syringe filter.

| Protocol K. | SE0K | 17% w/w |
| --- | --- | --- |
| | Lysine hydrochloride | 1:2 |
| | Cesium Carbonate | pH 9.5 |
| | Isocyanate:Amine | 14.5:1 |

The steps of Protocol B were followed, except that the stock buffer solution was prepared by dissolving lysine hydrochloride, 42.7 mg, in deionized water, 10.0 mL, and adding cesium carbonate, 55.2 mg, to pH 9.52. Evans Blue dye, 0.50 mg/mL, was dissolved in this buffer, and the solution filtered through a 0.45 micron syringe filter.

| Protocol L. | SE0K | 17% w/w |
| --- | --- | --- |
| | Lysine hydrochloride | 1:2 |
| | Calcium Carbonate | 1:1 |
| | Isocyanate:Amine | 14.5:1 |

The steps of Protocol B were followed, except that the stock buffer solution was prepared by dissolving lysine hydrochloride, 20.8 mg, in deionized water, 10.0 mL, and adding calcium carbonate, 68.6 mg. Evans Blue dye, 0.50 mg/mL, was dissolved in this buffer, and the solution filtered through a 0.45 micron syringe filter.

| Protocol M. | SE0K | 17% w/w |
| --- | --- | --- |
| | Lysine hydrochloride | 1:2 |
| | Potassium Carbonate | pH 9.0 |
| | Isocyanate:Amine | 14.5:1 |

The steps of Protocol B were followed, except that the stock buffer solution was prepared by dissolving lysine hydrochloride, 103.9 mg, in deionized water, 50.0 mL, and adding potassium carbonate, 473.3 mg. Using concentrated hydrochloric acid, this buffer was adjusted to pH 9.00.

| Protocol N1. | SE0K | 17% w/w |
| --- | --- | --- |
| | Lysine hydrochloride | 1:2 |
| | Potassium Carbonate | 1:1 |
| | Isocyanate:Amine | 14.5:1 |
| | Iodide:Carbonate | 1:2 |

The steps of Protocol B were followed, except that potassium iodide, 5.70 mg/mL was added to the stock buffer solution. The nominal pH of this dope was about pH 11.

| Protocol N2. | SE0K | 17% w/w |
| --- | --- | --- |
| | Lysine hydrochloride | 1:2 |
| | Potassium Carbonate | pH 9.0 |
| | Isocyanate:Amine | 14.5:1 |
| | Iodide:Carbonate | 1:2 |

The steps of Protocol B were followed, except that potassium iodide, 5.70 mg/mL was added to the stock buffer solution. Using concentrated hydrochloric acid, this buffer was adjusted to pH 9.00.

| Protocol O1. | SE0K | 17% w/w |
| --- | --- | --- |
| | Lysine hydrochloride | 1:2 |
| | Potassium Carbonate | 1:1 |
| | Isocyanate:Amine | 14.5:1 |
| | Glucose | 1.09 M |

The steps of Protocol B were followed, except that glucose, 1.2755 g, was added to the stock buffer solution, 6.495 mL. This solution was pH 10.5.

| Protocol O2. | SE0K | 17% w/w |
| --- | --- | --- |
| | Lysine hydrochloride | 1:2 |
| | Potassium Carbonate | pH 9.0 |
| | Isocyanate:Amine | 14.5:1 |
| | Glucose | 1.09 M |

The steps of Protocol B were followed, except that glucose, 1.2755 g, was added to the stock buffer solution, 6.495 mL. Using concentrated hydrochloric acid, this buffer was adjusted to pH 9.00.

| Protocol P1. | SE0K | 17% w/w |
| --- | --- | --- |
| | Lysine hydrochloride | 1:2 |
| | Potassium Carbonate | 1:1 |
| | Isocyanate:Amine | 14.5:1 |
| | Urea | 1.5 M |

The steps of Protocol B were followed, except that urea, 0.5226 g, was added to the stock buffer solution, 5.807 mL, nominally 1.5 M. This solution was pH 11.

| Protocol P2. | SE0K | 17% w/w |
| --- | --- | --- |
| | Lysine hydrochloride | 1:2 |
| | Potassium Carbonate | pH 9.00 |
| | Isocyanate:Amine | 14.5:1 |
| | Urea | 1.5 M |

The steps of Protocol B were followed, except that urea, 0.5226 g, was added to the stock buffer solution, 5.807 mL. Using concentrated hydrochloric acid, this buffer was adjusted to pH 9.00.

| Protocol Q. | SE0K | 17% w/w |
| --- | --- | --- |
| | Lysine hydrochloride | 1:2 |
| | Potassium carbonate | 1:1 |
| | Isocyanate:Amine | 7.3 |

The steps of Protocol B were followed, except that the volume of the HMDI setting agent was reduced to 1.0 µL.

| Protocol R. | SE0K | 17% w/w |
| --- | --- | --- |
| | Lysine hydrochloride | 1:2 |
| | Potassium carbonate | 1:1 |
| | Isocyanate:Amine | 6.7; 6.5; 6.1:1 |

The steps of Protocol B were followed, except that the HMDI setting agent was diluted 1.1 w/w, 1:3 w/w, or 1:5 w/w with toluene. The volume of diluted HMDI setting agent applied to the lap joint was 2 µL, 4 µL, or 6 µL, respectively.

| Protocol S. | SE0K | 17% w/w |
| --- | --- | --- |
| | Lysine hydrochloride | 1:2 |
| | Potassium carbonate | 1:1 |
| | Isocyanate:Amine | 6.1; 5.7; 5.6:1 |

The steps of Protocol B were followed, except that the HMDI setting agent was diluted 1:1 w/w, 1:3 w/w, or 1:5 w/w with methylcyclohexane. The volume of diluted HMDI setting agent applied to the lap joint was 2 µL, 4 µL, or 6 µL, respectively.

| Protocol T. | SE0K | 17% w/w |
| --- | --- | --- |
| | Lysine hydrochloride | 1:2 |
| | Potassium carbonate | 1:1 |
| | Isocyanate:Amine | 8.5; 9.4; 9.7:1 |

The steps of Protocol B were followed, except that the HMDI setting agent was diluted 1:1 w/w, 1:3 w/w, or 1:5 w/w with chloroform. The volume of diluted HMDI setting agent applied to the lap joint was 2 µL, 4 µL, or 6 µL, respectively.

| Protocol U. | SE0K | 17% w/w |
| --- | --- | --- |
| | Lysine hydrochloride | 1:2 |
| | Potassium carbonate | 1:1 |
| | Isocyanate:Amine | 8.0; 8.7; 7.8:1 |

The steps of Protocol B were followed, except that the HMDI setting agent was diluted 1:1 w/w, 1:3 w/w, or 1:5 w/w with methylene chloride. The volume of diluted HMDI setting agent applied to the lap joint was 2 µL, 4 µL, or 6 µL, respectively.

| Protocol V1. | SE8K | 33% w/w |
| --- | --- | --- |
| | Lysine hydrochloride | 1:1 |
| | Potassium carbonate | 3:2 |
| | Isocyanate:Amine | 5.0:1 |

Preparation of Protein Dope

A stock solution of buffer was prepared by dissolving lysine hydrochloride, 9.14 mg/mL, potassium carbonate 41.6 mg/mL, and Evans Blue dye, 0.50 mg/mL deionized water. The mixture was filtered through a glass wool plug before use. SE8K, 113.9 mg, and 227.8 mg of stock buffer were placed in a Eppendorf vial and agitated on a vortex mixer until dissolved. Bubbles were removed from this solution by centrifugation at 5000 rpm for 30 seconds. This protein dope solution was then loaded into a 1.00 mL syringe and let stand for 20 minutes at room temperature before dispensing to the lap joint test specimens.

Preparation of HMDI Setting Agent

The HMDI setting agent was prepared by dissolving Sudan Red dye, 3.75 mg, in Pluronic surfactant L-61, and adding an equal weight of 1,6-diisocyanatohexane.

Preparation of Rat Skins

Freshly harvested rat hides were stored frozen at −20° C. Just before use the hides were thawed and cut into 1 cm×3 cm strips. Strips were selected which were uniform in width and thickness and which were devoid of loose fascia and muscle tissue. These rat skin samples were temporarily stored at 37° C. between gauze pads soaked with PBS and contained in a plastic bag to prevent drying prior to use.

Application of Adhesive

Protein dope, 35 µL, was applied to one end of a rat skin and worked into about a 1 cm² area with 5-10 strokes of a stainless steel spatula. The excess protein dope was transferred with the stainless steel spatula to the second strip of rat skin and worked in similarity. A total of 3.8 μL of HMDI setting agent was applied to the skins, apportioned so that 3 parallel stripes of HMDI were applied to the first skin. The skins were immediately assembled to form the lap joint, rubbed against each other to distribute the HMDI setting agent, covered with a piece of plastic film to prevent drying, and compressed under a 100 g weight. The joint was allowed to cure for 15 minutes at 37° C. The length and width of the lap joint was measured to 1 mm using a ruler immediately before tensile testing on an Instron Model 55 test machine. The crosshead speed was set at 25 mm per minute. Lap shear tensile strengths were reported in units of g/cm². Means and standard deviations were calculated for measurements conducted at least in triplicate.

| Protocol V2. | SE8K | 33% w/w |
| --- | --- | --- |
| | Lysine hydrochloride | 1:2 |
| | Potassium carbonate | 3:2 |
| | Isocyanate:Amine | 5.0:1 |

The method of Protocol VI was followed except that a stock solution of buffer was prepared by dissolving lysine hydrochloride, 4.59 mg/mL, potassium carbonate 31.2 mg/mL, and Evans Blue dye, 0.50 mg/mL in deionized water.

| Protocol V3. | SE8K | 33% w/w |
| --- | --- | --- |
| | Lysine hydrochloride | 0:2 |
| | Potassium carbonate | 3:2 |
| | Isocyanate:Amine | 5.0:1 |

The method of Protocol Vi was followed except that a stock solution of buffer was prepared by dissolving potassium carbonate 13.83 mg/mL, and Evans Blue dye, 0.50 mg/mL in deionized water.

| Protocol W1. | SE0K | 17% w/w |
| --- | --- | --- |
| | Arginine | 1:4 |
| | Potassium carbonate | 1.2:1 |
| | Isocyanate:Amine | 13.1:1 |

The method of Protocol A was followed except that the buffer was prepared using arginine, 2.4 mg/mL, potassium carbonate, 9.46 mg/mL, and Evans Blue dye, 0.50 mg/mL in deionized water. The volume of HMDI setting agent applied to the lap joint was 2.0 μL. Only the alpha amino group of the arginine is assume to participate in the stoichoimetry of the setting reaction.

| Protocol W2. | SE0K | 17% w/w |
| --- | --- | --- |
| | Cysteine | 1:2 |
| | Potassium carbonate | 1:1 |
| | Isocyanate:Amine | 13.1:1 |

The method of Protocol A was followed except that the buffer was prepared using cysteine, 1.38 mg/mL, and potassium carbonate, 9.46 mg/mL, and Evans Blue dye, 0.50 mg/mL in deionized water. The volume of HMDI setting agent applied to the lap joint was 2.0 μL.

| Protocol W3. | SE0K | 17% w/w |
| --- | --- | --- |
| | Tyrosine | 1:2 |
| | Potassium carbonate | 1:1 |
| | Isocyanate:Amine | 13.1:1 |

The method of Protocol A was followed except that the buffer was prepared using tyrosine, 2.07 mg/mL, and potassium carbonate, 9.46 mg/mL, and Evans Blue dye, 0.50 mg/mL in deionized water. The volume of HMDI setting agent applied to the lap joint was 2.0 μL.

| Protocol W4. | SE0K | 17% w/w |
| --- | --- | --- |
| | 1,3-BDSA | 1:2 |
| | Potassium carbonate | 1:1 |
| | Isocyanate:Amine | 13.1:1 |

The method of Protocol A was followed except that the buffer was prepared using 1,3-benzene disulfonic acid disodium salt monohydrate (1,3-BDSA), 3.79 mg/mL, and potassium carbonate, 9.46 mg/mL, and Evans Blue dye, 0.50 mg/mL in deionized water. The volume of HMDI setting agent applied to the lap joint was 2.0 μL.

| Protocol X. | SE0K | 17% w/w |
| --- | --- | --- |
| | Peptide RGRGRGKGKGK | 1:2 (SEQ ID NO:35) |
| | Potassium carbonate | 1:1 |
| | Isocyanate:Amine | 14.5:1 |

The method of Protocol A was followed except that the buffer was prepared using synthetic peptide RGRGRGKGKGK (SEQ ID NO:35), 4.4 mg/mL, potassium carbonate, 9.46 mg/mL, and Evans Blue dye, 0.50 mg/mL in deionized water. The volume of HMDI setting agent applied to the lap joint was 2.0 μL.

| Protocol Y. | SE0K | 17% w/w |
| --- | --- | --- |
| | Cholinyl lysinate | 1:4 |
| | Potassium carbonate | 1.12:1 |
| | Isocyanate:Amine | 14.5:1 |

The method of Protocol B was followed except that the buffer was prepared by dissolving cholinyl lysinate, 29.2 mg, potassium carbonate, 123.9 mg, and Evans Blue dye, 6.0 mg, in deionized water, 13.09 mL. The buffer solution was filtered through a 0.45 micron syringe filter before use. The protein dope was prepared by dissolving SE0K, 63.5 mg, in 310.0 μL of buffer.

| Protocol Z. | SE0K | 17% w/w |
| --- | --- | --- |
| | AEGly | 1:4 |
| | Potassium carbonate | 1:1 |
| | Isocyanate:Amine | 14.5:1 |

The method of Protocol B was followed except that the buffer was prepared using 2-aminoethyl glycinate, AEGly (see Example 1, diamine synthesis). An aliquot, 28.9 mg, of 2-aminoethyl glycinate in water, 236 mg/mL, and potassium carbonate, 48.6 mg, was dissolved in water, 5.127 mL.

Evans Blue dye, 2.20 mg was added, and the solution filtered through a 0.45 micron syringe filter.

| Protocol AA. | SE8K | 17% w/w |
|---|---|---|
| | Lysine hydrochloride | 1:1 |
| | Potassium carbonate | 1:1 |
| | Isocyanate:Amine | 12.0:1 |

The method of Protocol V1 was followed except that the buffer was prepared using lysine hydrochloride, 3.73 mg/mL, potassium carbonate, 11.33 mg/mL, and Evans Blue dye, 0.50 mg/mL in deionized water. Pluronic surfactant L-61 was not added to the HMDI setting agent. The protein polymer used was SE8K. The volume of setting agent applied to the joint was 2.0 µL.

| Protocol AB. | SE0K-CS1 | 17% w/w |
|---|---|---|
| | Lysine hydrochloride | 0.94:2 |
| | Potassium carbonate | 0.96:1 |
| | Isocyanate:Amine | 16.4:1 |

The method of Protocol A was followed except that the buffer was prepared using lysine hydrochloride, 1.84 mg/mL, potassium carbonate, 8.37 mg/mL, and Evans Blue dye, 0.50 mg/mL in deionized water. The protein polymer used was SE0K-CS1. The volume of setting agent applied to the joint was 2.0 µL.

| Protocol AC. | SE0K | 17% w/w |
|---|---|---|
| | Lysine hydrochloride | 1:2 |
| | Sodium Borate | pH 9.5 |
| | Isocyanate:Amine | 7.3:1 |

The steps of Protocol F were followed, except that the volume of HMDI setting agent applied to the lap joint was 1.0 µL.

| Protocol AD. | SE0K | 17% w/w |
|---|---|---|
| | Lysine hydrochloride | 1:2 |
| | Sodium Borate | pH 9.5 |
| | Isocyanate: Amine | 7.3:1 |

The steps of Protocol F were followed, except that the HMDI setting agent was diluted 1:1 v/v, 1:3 v/v, or 1:5 v/v using cyclohexane. The volume of diluted HMDI setting agent applied to the lap joint was 2 µL, 4 µL, or 6 µL, respectively.

| Protocol AE. | SE0K | 17% w/w |
|---|---|---|
| | Lysine hydrochloride | 1:2 |
| | Sodium Borate | pH 9.5 |
| | Isocyanate:Amine | 7.3:1 |

The steps of Protocol F were followed, except that the HMDI setting agent was diluted 1:1 v/v, 1:3 v/v, or 1:5 v/v using 1,1,1-trichloroethane. The volume of diluted HMDI setting agent applied to the lap joint was 2 µL, 4 µL, or 6 µL, respectively.

| Protocol AF. | SE0K | 17% w/w |
|---|---|---|
| | Lysine hydrochloride | 1:2 |
| | Sodium Borate | pH 9.5 |
| | Isocyanate:Amine | 7.3:1 |

The steps of Protocol F were followed, except that the HMDI setting agent was diluted 1:1 v/v, 1:3 v/v, 1:5 v/v, or 1:9 v/v using ethyl acetate. The volume of diluted HMDI setting agent applied to the lap joint was 2 µL, 4 µL, 6 µL, or 10 µL, respectively.

| Protocol AG. | SE0K-CS1 | 17% w/w |
|---|---|---|
| | 1,3-PG | 0.39:2 |
| | Potassium carbonate | 0.496:1 |
| | Potassium bicarbonate | 0.496:1 |
| | Isocyanate:Amine | 2.5:1 |

The methods of Protocol B were followed with the following modifications.

Preparation of Protein Dope

Protein polymer SE0K-CS1, 81.6 mg, was added to 311 µL of deionized water in an Eppendorf tube and agitated on a vortex mixer until dissolved. To this solution was added 11.43 µL of a solution of 1,3-propanediyldiglycinate (1,3-PG) in water, 10% w/w; 14.73 µL of a solution of potassium carbonate in water, 10% w/w; and 9.43 µL of a solution of potassium bicarbonate in water, 10% w/w. The contents were again agitated on the vortex mixer until homogeneous. The solution was centrifuged at about 5000 rpm for 30-60 seconds to separate air bubbles, and then the dope was exposed to reduced pressure, 26 in-Hg, for 30 minutes.

Preparation of HMDI Setting Agent

Neat 1,6-diisocyanatohexane, 100 mg, and Sudan Red dye, 2.4 mg, were dissolved in 1-chloro-2,2,2-trifluoroethyl diflurormethyl ether, 2.342 g. The volume of diluted HMDI setting agent applied to the lap joint was 4 µL.

| Protocol AH. | SE0K | 17% w/w |
|---|---|---|
| | Lysine | 0:1 |
| | Potassium carbonate | 1:1 |
| | Isocyanate:Amine | 5.0:1 |

Preparation of Protein Dope

Protein dope was prepared by dissolving protein polymer SE0K at 17% w/w in 10 mMolar aqueous lactic acid, 0.90 mg/mL. This protein dope tested approximately pH 3.5 with wide range pH test paper. A solution to initiate curing was prepared by dissolving potassium carbonate, 1.66 g, in deionized water, 10 mL.

Preparation of HMDI Setting Agent

An HMDI setting agent was prepared by dissolving 1,6-diisocyanatohexane, 5.04 g, Pluronic surfactant F-127, 0.0033 g, and Sudan Red dye, 0.0020 g in chloroform, 2.24 g.

Preparation of Rat Skins

Freshly harvested rat hides were stored frozen at −20° C. Just before use the hides were thawed and cut into 1 cm×3 cm strips. All fascia was removed from the strips of skin with a razor blade. Strips of skin were selected which were uniform in width and thickness. Prepared rat skin samples were temporarily stored at 37° C. between gauze pads soaked with PBS and contained in a plastic bag to prevent drying.

Application of Adhesive

The strips of skins were arranged on a glass plate in a 37° C. warm room. Protein dope, 15 μL, was worked into an approximately 1 cm² area at the end of each of two rat skins using a stainless steel spatula, 30 μL total. The HMDI setting agent, 1.0 μL, was worked into an approximately 1 cm² area at the end of each of two rat skins using a stainless steel spatula, 2.0 μL total. The potassium carbonate curing solution, 2.0 μL, was added as 6 drops, 3 drops applied to each of the two rat skins and the skins immediately assembled to form a lap joint. A 100 g weight was applied to the joint and the adhesive allowed to cure for 15 minutes at 37° C. The lap joint was tested to failure on an Instron tensile testing machine as described herein.

The first study employed the surfactant Pluronic L-31.

TABLE 18

Role of Pluronic L-31 Surfactant.

| | SEOK Dope | $K_2CO_3$ | L-Lys | HMDI + Pluronic | Lap Shear g/cm² | Protocol |
|---|---|---|---|---|---|---|
| 1 | SEOK 17% w/w | 1:1 | 1:2 | none | 2143 ± 328 | A |
| 2 | SEOK 17% w/w (degassed) | 1:1 | 1:2 | none | 2901 ± 685 | B |
| 3 | SEOK 17% w/w (degassed) | 1:1 | 1:2 | HMDI/L-31 1:1 (3.3% w/w wrt total dope) | 1248 ± 370 | C |
| 4 | SEOK 17% w/w (degassed) + L-31 (1.04% w/w wrt total dope) | 1:1 | 1:2 | none | 745 ± 209 | D1 |
| 5 | SEOK 17% w/w (degassed) + L-31 (0.24% w/w wrt total dope) (1.4% w/w wrt SEOK) | 1:1 | 1:2 | none | 1499 ± 159 | D2 |
| 6 | SEOK 17% w/w (degassed) + L-31 (0.17% w/w wrt total dope) (1.0% w/w wrt SEOK) | 1:1 | 1:2 | HMDI/ L-31 1:1 (3.3% w/w wrt total dope) | 677 ± 284 | E |

In the next sudy, various buffers were employed in conjunction with lysine as the polyfunctional group.

TABLE 19

Adhesive Performance Using 17% SELP0K (SE0K) in Various Buffers at pH 9.5.

| | Buffer | Lap Shear g/cm² | CV % | Protocol |
|---|---|---|---|---|
| 1 | $Na_3BO_3$/L-Lys (1:2)* | 2360 ± 475 | 20% | F |
| 2 | $K_3BO_3$/L-Lys (1:2) | 2037 ± 338 | 17% | G |
| 3 | $Li_2CO_3$/L-Lys (1:2) | 188 ± 38 | 20% | H |
| 4 | $Na_2CO_3$/L-Lys (1:2) | 1168 ± 274 | 23% | I |
| 5 | $K_2CO_3$/L-Lys (1:2) | 2393 ± 631 | 26% | J |
| 6 | $Cs_2CO_3$/L-Lys (1:2) | 233 ± 56 | 24% | K |
| 7 | $CaCO_3$/L-Lys (1:2) | 88 ± 2 | 2% | L |

*The mole ratio of amino groups derived from lysine to amino groups derived from SELP0K.

In the next study various chemically unreactive and reactive additives were added to the formulation to determine the effect of the additives on shear strength.

TABLE 20

Adhesive Performance Using 17% SELP0K in Carbonate Buffers with Additives

| | Buffer | pH | Lap Shear g/cm² | CV | Protocol |
|---|---|---|---|---|---|
| 1 | $K_2CO_3$ (2:2)/L-Lys (1:2) | 10.5 | 2901 ± 685 | 24% | B |
|   | no additive | 9.0 | 1617 ± 293 | 18% | M |
| 2 | $K_2CO_3$ (2:2)/L-Lys (1:2) plus KI (0.043 Mole/L) | 11 | 2538 ± 441 | 17% | N1 |
|   |  | 9.0 | 826 ± 211 | 26% | N2 |
| 3 | $K_2CO_3$ (2:2)/L-Lys (1:2) plus Glucose (1.09 Mole/L) | 10.5 | 1896 ± 557 | 29% | O1 |
|   |  | 9.0 | 1398 ± 358 | 26% | O2 |
| 4 | $K_2CO_3$ (2:2)/L-Lys (1:2) plus Urea (1.50 Mole/L) | 11 | 2674 ± 846 | 32% | P1 |
|   |  | 9.0 | 239 ± 38 | 16% | P2 |

In the next study various organic solvents were employed, where the crosslinking agent was dissolved in the solvent prior to mixing with the aqueous buffered protein solution.

TABLE 21

Adhesive Performance Using HMDI Plus Volatile Diluents with 17% SELP0K in Lysine-Borate Buffer pH 9.5.

| | Diluent | bp | Dilution Ratio [v/v] | Setting Agent Volume | Lap Shear g/cm² | CV % | Protocol |
|---|---|---|---|---|---|---|---|
| 1 | None | n.a. | 1:0 | 1 μL | 852 ± 173 | 20% | AC |
| 2 | Cyclohexane | 81° | 1:1 | 2 μL | 900 | n.a. | AD |
|   |  |  | 1:3 | 4 μL | 953 |  |  |
|   |  |  | 1:5 | 6 μL | 1053 |  |  |
| 3 | 1,1,1-Trichloro-ethane | 75° | 1:1 | 2 μL | 781 ± 13 | 2% | AE |
|   |  |  | 1:3 | 4 μL | 943 ± 119 | 13% |  |
|   |  |  | 1:5 | 6 μL | 816 ± 51 | 6% |  |
| 4 | Ethyl Acetate | 77° | 1:1 | 2 μL | 869 ± 41 | 5% | AF |
|   |  |  | 1:3 | 4 μL | 741 ± 296 | 40% |  |
|   |  |  | 1:5 | 6 μL | 685 ± 147 | 21% |  |
|   |  |  | 1:9 | 10 μL | 658 ± 131 | 20% |  |

TABLE 22

Adhesive Performance Using HMDI Plus Volatile Diluents with 17% SELP0K in Lysine-Carbonate Buffer pH 10.

| | Diluent | bp | Ratio [w/w] | Setting agent Volume | Lap Shear g/cm² | CV % | Protocol |
|---|---|---|---|---|---|---|---|
| 1 | None | n.a. | 1:0 | 1 µL | 2713 ± 234 | 6% | Q |
| 2 | Toluene | 110° | 1:1 | 2 µL | 2303 ± 502 | 22% | R |
| | | | 1:3 | 4 µL | 2295 ± 210 | 9% | |
| | | | 1:5 | 6 µL | 1178 ± 282 | 24% | |
| 3 | Methyl Cyclohexane | 101° | 1:1 | 2 µL | 2508 ± 234 | 9% | S |
| | | | 1:3 | 4 µL | 2160 ± 111 | 5% | |
| | | | 1:5 | 6 µL | 1364 ± 395 | 29% | |
| 4 | Chloroform | 61° | 1:1 | 2 µL | 2075 ± 370 | 18% | T |
| | | | 1:3 | 4 µL | 2836 ± 620 | 22% | |
| | | | 1:5 | 6 µL | 1493 ± 223 | 15% | |
| 5 | Methylene Chloride | 40° | 1:1 | 2 µL | 2389 ± 542 | 23% | U |
| | | | 1:3 | 4 µL | 2636 ± 504 | 19% | |
| | | | 1:5 | 6 µL | 2511 ± 493 | 20% | |

In the next study various polyfunctional agents were employed using a variety of functionalities to crosslink the polymer, where the functionalities were symmetrical or unsymmetrical and the intervening chains were aliphatic or aromatic, with different functional groups as side chains. In some instances, the polyfunctional agents used for crosslinking were hydrolytically unstable, having a hydrolytically susceptible bond in the linking chain.

TABLE 23

Adhesive Performance Using SELP8K, SELP0K or SELP0K-CS1 With Different Polyfunctional Agents

| Protein and Buffer | Ratio* | Polyfunctional Agent | Lap Shear Tensile g/cm² | Protocol |
|---|---|---|---|---|
| SE8K 33% w/w K₂CO₃ 3:2 | 2:2 | Lysine | 1328 ± 203 | V1 |
| | 1:2 | | 1212 ± 241 | V2 |
| | 0:2 | | 1161 ± 383 | V3 |
| SE0K 17% w/w K₂CO₃ 1:1 | 1:2 | Lysine | 2143 ± 328 | A |
| | | Arginine | 1176 ± 748 | W1 |
| | | Cysteine | 741 ± 66 | W2 |
| | | Tyrosine | 622 ± 339 | W3 |
| | | 3,5-Disulfonato-catechol | 399 | W4 |
| SE0K 17% w/w K₂CO₃ 1:1 | 1:2 | Peptide RGRGRGKGKGK | 850 ± 184 | X |
| SE0K 17% w/w K₂CO₃ 1:1 | 1:2 | Lysine | 2901 ± 685 | B |
| SE0K 17% w/w K₂CO₃ 1.12:1 | 1:4 | cholinyl lysinate | 2385 ± 502 | Y |
| SE0K 17% w/w K₂CO₃ 1.12:1 | 1:4 | 2-aminoethyl glycinate N,O-Diglycyl ethanolamine 4:1 mixture as sulfate salt | 3269 ± 422 | Z |
| SE0K-CS1 17% w/w K₂CO₃ 1:1 | 1:2 | Lysine | 2196 ± 275 | AB |
| SE0K-CS1 17% w/w K₂CO₃ 1:1 | 0.77:2 | 1,3-Propanediyl Diglycinate | 3028 ± 392 | AG |

*Ratio of added nucleophilic groups to amino groups available on the protein backbone.

In Table 24, various formulations comprising either SELP8K, SELP0K, SELP0K-CS1 are compared.

TABLE 24

Adhesive Performance Using SELP8K, SELP0K, and SELP0K-CS1.

| Polymer | K₂CO₃ to Amine Ratio | Amine Ratio* | Lap Shear Tensile g/cm² | % CV | Protocol |
|---|---|---|---|---|---|
| SE8K 17% w/w | 1:1 | 2:2 | 2854 ± 1027 | 36% | AA |
| SE0K 17% w/w | 1:1 | 1:2 | 2143 ± 328 | 15% | A |
| SE0K 17% w/w in 10 mM aq. Lactic Acid | 1:1 | 0:2 | 532 ± 207 | 39% | AH |
| SE0K-CS1 17% w/w | 1:1 | 1:2 | 2196 ± 275 | 13% | AB |

*Ratio of amine groups derived from lysine to amine groups derived from the protein.

It is evident from the above results, that the subject invention provides for compositions which can set rapidly to provide compositions having a broad range of properties. The subject compositions can provide for strongly adhering compositions with good shear strength, the shear strength being realized within a short period of time. The subject invention also provides for compositions that are capable of filling voids or holes in tissue or otherwise augmenting the tissue. Thus, the subject proteinaceous polymers may be employed as tissue adhesives, providing physiologically compatible compositions which maintain their strength for extended periods of time, while being capable of resorption, as well as sealants, among other uses.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A kit comprising a protein block copolymer of at least 30 kD comprising at least 70 weight % of repetitive units of GAGAGS (SEQ ID NO:01) and GVGVP (SEQ ID NO:02), where in at least two units an amino acid is substituted with at least one of lysine or arginine, said copolymer having a lysine and arginine equivalent weight in the range of 1 to 40 kD and a crosslinking agent selected from the group consisting of glutaraldehyde and aliphatic diisocyanates.

2. A method of maintaining separated viable tissue in proximate relationship, said method comprising:

applying a precursor composition to said separated viable tissue to hold together said tissue when said separated tissue is in contiguous relationship, said precursor composition comprising (1) a polyfunctional crosslinking agent comprising 2-aminoethyl glycinate, cholinyl lysinate or 1,3-propanediyl glycinate reacted with a difunctional compound which reacts with amino groups, and (2) a protein polymer comprising at least 40 weight % of repetitive units of from 3 to 15 amino acids of at least one naturally occurring structural protein, where there are at least two amino functional groups present in said protein polymer, which amino functional groups react with said crosslinking agent, whereby said precursor composition sets up to a strongly adherent adhesive composition;

with said separated viable tissue held in proximate relationship.

3. A method of sealing a defect in viable tissue, said method comprising:

applying to said defect a precursor composition comprising a polyfunctional crosslinking agent selected from the group consisting of glutaraldehyde and polymethylene diisocyanate and a protein polymer comprising at least 40 weight % of repetitive units of from 3 to 15 amino acids of at least one naturally occurring structural protein wherein at least two amino acids of said protein polymer are substituted with lysine or arginine, whereby said precursor composition sets up to a strongly adherent adhesive composition;

whereby said defect is sealed.

4. A method according to claim 3, wherein said units are selected from the group consisting of GAGAGS (SEQ ID NO:01), GVGVP (SEQ ID NO:02) and GXX, wherein the X's are the same or different and X is any amino acid, at least 10 number % and not more than 60 number % of X's being proline.

5. A method according to claim 3, wherein said units are GAGAGS (SEQ ID NO:01) and GVGVP (SEQ ID NO:02) and are present to form a block copolymer protein.

6. A method according to claim 3, wherein said tissue is the wall of a vessel selected from an artery, vein, capillary, lung, dura or colon.

7. A method of maintaining separated viable tissue in proximate relationship, said method comprising:

applying a precursor composition to said separated viable tissue to hold said tissue together when said separated tissue is in contiguous relationship, said precursor composition comprising a polyfunctional crosslinking agent selected from the group consisting of glutaraldehyde and polymethylene diisocyanate and a protein block copolymer of at least 30 kD comprising at least 70 weight % of repetitive units of GAGAGS (SEQ ID NO:01) and GVGVP (SEQ ID NO:02), where in at least two units an amino acid is substituted with at least one of lysine or arginine, said copolymer having a lysine and arginine equivalent weight in the range of 3 to 15 kD, whereby said precursor composition sets up to a strongly adherent adhesive composition;

with said separated viable tissue held in proximate relationship.

* * * * *

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

```
Gly Ala Gly Ala Gly Ser
1               5
```

(2) INFORMATION FOR SEQ ID NO: 2:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

```
Gly Val Gly Val Pro
1               5
```

(2) INFORMATION FOR SEQ ID NO: 3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
Ala Lys Leu Xaa Leu Ala Glu
1               5
```

(2) INFORMATION FOR SEQ ID NO: 4:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Gly Ala Gly Ala Gly Ser Gly Ala Gly Ala Ser Gly Ala Gly Ala
1               5                   10                  15

Gly Ser Gly Ala Gly Ala Gly Ser Gly Val Gly Val Pro Gly Val
                20                  25                  30

Val Pro Gly Val Gly Val Pro Gly Val Gly Val Pro Gly Lys Gly Val
            35                  40                  45

Pro Gly Val Gly Val Pro Gly Val Gly Val Pro Gly Val Gly Val Pro
    50                  55                  60
```

(2) INFORMATION FOR SEQ ID NO: 5:

(i) SEQUENCE CHARACTERISTICS:
        (A) LENGTH: 64 amino acids
        (B) TYPE: amino acid (C) STRANDEDNESS: single
        (D) TOPOLOGY: linear (ii) MOLECULE TYPE: peptide (xi) SEQUENCE DESCRIPTION: SEQ ID NO: 5:

Gly Ala Gly Ala Gly Ser Gly Ala Gly Ala Gly Ser Gly Ala Gly Ala
1               5                   10                  15

Gly Ser Gly Ala Gly Ala Gly Ser Gly Val Gly Val Pro Gly Val Gly
            20                  25                  30

Val Pro Gly Val Gly Val Pro Gly Val Gly Val Pro Gly Glu Gly Val
        35                  40                  45

Pro Gly Val Gly Val Pro Gly Val Gly Val Pro Gly Val Gly Val Pro
    50                  55                  60

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

CTGGAGCGGG TGCCTGCATG TACATCCGAG T                               31

(2) INFORMATION FOR SEQ ID NO: 7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

ACTCGGATGT ACATGCAGGC ACCCGCTCCA GAGCC                           35

(2) INFORMATION FOR SEQ ID NO: 8:

(i) SEQUENCE CHARACTERISTICS:
        (A) LENGTH: 192 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 8:

GGTGCCGGTT CTGGAGCTGG CGCGGGCTCT GGAGTAGGTG TGCCAGGTGT AGGAGTTCCG    60

GGTGTAGGCG TTCCGGGAGT TGGTGTACCT GGAGTGGGTG TTCCAGGCGT AGGTGTGCCC   120

GGGGTAGGAG TACCAGGGGT AGGCGTGCCT GGAGCGGGTG CTGGTAGCGG CGCAGGCGCG   180

GGCTCTGGAG CG                                                      192

(2) INFORMATION FOR SEQ ID NO: 9:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Gly Ala Gly Ser Gly Ala Gly Ala Gly Ser Gly Val Gly Val Pro Gly
1               5                   10                  15

Val Gly Val Gly Pro Gly Val Gly Val Pro Gly Val Gly Val Pro Gly
            20                  25                  30

Val Gly Val Pro Gly Val Gly Val Pro Gly Val Gly Val Pro Gly Val
        35                  40                  45

Gly Val Pro Gly Ala Gly Ala Gly Ser Gly Ala Gly Ala Gly Ser Gly
    50                  55                  60

Ala

65

(2) INFORMATION FOR SEQ ID NO: 10:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

ATGGCAGCGA AAGGGGACCG GGCTCTGGTG TTGGAGTGCC AGGTGTCGGT GTTCCGGGTG    60

TAGGCGTTCC GGGAGTTGGT GTACCTGGAA AGGTGTTCCG GGGGTAGGTG TGCCGGGCGT   120

TGGAGTACCA GGTGTAGGCG TCCCGGGAGC GGGTGCTGGT AGCGGCGCAG GCGCGGGCTC   180

TTTCCGCTAA AGTCCTGCCG T    201

(2) INFORMATION FOR SEQ ID NO: 11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

AAGAAGGAGA TATCATATGG CAGCGAAAGG GGACC    35

(2) INFORMATION FOR SEQ ID NO: 12:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

CGCAGATCTT TAAATTACGG CAGGACTTTA GCGGAAA    37

(2) INFORMATION FOR SEQ ID NO: 13:

(i) SEQUENCE CHARACTERISTICS:
        (A) LENGTH: 192 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 13:

```
GGTGCCGGTT CTGGAGCTGG CGCGGGCTCT GGTGTTGGAG TGCCAGGTGT CGGTGTTCCG        60

GGTGTAGGCG TTCCGGGAGT TGGTGTACCT GGAAAAGGTG TTCCGGGGGT AGGTGTGCCG       120

GGCGTTGGAG TACCAGGTGT AGGCGTCCCG GGAGCGGGTG CTGGTAGCGG CGCAGGCGCG       180

GGCTCTGGAG CG                                                          192
```

(2) INFORMATION FOR SEQ ID NO: 14:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Gly Ala Gly Ser Gly Ala Gly Ala Gly Ser Gly Val Gly Val Pro Gly
1               5                   10                  15

Val Gly Val Pro Gly Val Gly Val Pro Gly Val Gly Val Pro Gly Lys
                20                  25                  30

Gly Val Pro Gly Val Gly Val Pro Gly Val Gly Val Pro Gly Val Gly
            35                  40                  45

Val Pro Gly Ala Gly Ala Gly Ser Gly Ala Gly Ala Gly Ser Gly Ala
        50                  55                  60
```

(2) INFORMATION FOR SEQ ID NO: 15:

(i) SEQUENCE CHARACTERISTICS:
        (A) LENGTH: 884 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala Gly Ser Gly Ala Gly Ala Gly Ser Gly Val Gly Val Pro
            35                  40                  45

Gly Val Gly Val Pro Gly Val Gly Val Pro Gly Val Gly Val Pro Gly
        50                  55                  60

Lys Gly Val Pro Gly Val Gly Val Pro Gly Val Gly Val Pro Gly Val
65                  70                  75                  80

Gly Val Pro Gly Ala Gly Ala Gly Ser Gly Ala Gly Ala Gly Ser Gly
                85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
        115                 120                 125

Lys Gly Val Pro Gly Val Gly Val Pro Gly Val Gly Val Pro Gly Val
130                 135                 140

Gly Val Pro Gly Ala Gly Ala Gly Ser Gly Ala Gly Ala Gly Ser Gly
145                 150                 155                 160
```

Ala Gly Ala Gly Ser Gly Ala Gly Ala Gly Ser Gly Val Gly Val Pro
            165                 170                 175

Gly Val Gly Val Pro Gly Val Gly Val Pro Gly Val Gly Val Pro Gly
            180                 185                 190

Lys Gly Val Pro Gly Val Gly Val Pro Gly Val Gly Val Pro Gly Val
            195                 200                 205

Gly Val Pro Gly Ala Gly Ala Gly Ser Gly Ala Gly Ala Gly Ser Gly
        210                 215                 220

Ala Gly Ala Gly Ser Gly Ala Gly Ala Gly Ser Gly Val Gly Val Pro
225                 230                 235                 240

Gly Val Gly Val Pro Gly Val Gly Val Pro Gly Val Gly Val Pro Gly
            245                 250                 255

Lys Gly Val Pro Gly Val Gly Val Pro Gly Val Gly Val Pro Gly Val
            260                 265                 270

Gly Val Pro Gly Ala Gly Ala Gly Ser Gly Ala Gly Ala Gly Ser Gly
        275                 280                 285

Ala Gly Ala Gly Ser Gly Ala Gly Ala Gly Ser Gly Val Gly Val Pro
        290                 295                 300

Gly Val Gly Val Pro Gly Val Gly Val Pro Gly Val Gly Val Pro Gly
305                 310                 315                 320

Lys Gly Val Pro Gly Val Gly Val Pro Gly Val Gly Val Pro Gly Val
            325                 330                 335

Gly Val Pro Gly Ala Gly Ala Gly Ser Gly Ala Gly Ala Gly Ser Gly
            340                 345                 350

Ala Gly Ala Gly Ser Gly Ala Gly Ala Gly Ser Gly Val Gly Val Pro
            355                 360                 365

Gly Val Gly Val Pro Gly Val Gly Val Pro Gly Val Gly Val Pro Gly
            370                 375                 380

Lys Gly Val Pro Gly Val Gly Val Pro Gly Val Gly Val Pro Gly Val
385                 390                 395                 400

Gly Val Pro Gly Ala Gly Ala Gly Ser Gly Ala Gly Ala Gly Ser Gly
            405                 410                 415

Ala Gly Ala Gly Ser Gly Ala Gly Ala Gly Ser Gly Val Gly Val Pro
            420                 425                 430

Gly Val Gly Val Pro Gly Val Gly Val Pro Gly Val Gly Val Pro Gly
            435                 440                 445

Lys Gly Val Pro Gly Val Gly Val Pro Gly Val Gly Val Pro Gly Val
        450                 455                 460

Gly Val Pro Gly Ala Gly Ala Gly Ser Gly Ala Gly Ala Gly Ser Gly
465                 470                 475                 480

Ala Gly Ala Gly Ser Gly Ala Gly Ala Gly Ser Gly Val Gly Val Pro
            485                 490                 495

Gly Val Gly Val Pro Gly Val Gly Val Pro Gly Val Gly Val Pro Gly
            500                 505                 510

Lys Gly Val Pro Gly Val Gly Val Pro Gly Val Gly Val Pro Gly Val
            515                 520                 525

Gly Val Pro Gly Ala Gly Ala Gly Ser Gly Ala Gly Ala Gly Ser Gly
        530                 535                 540

Ala Gly Ala Gly Ser Gly Ala Gly Ala Gly Ser Gly Val Gly Val Pro
545                 550                 555                 560

Gly Val Gly Val Pro Gly Val Gly Val Pro Gly Val Gly Val Pro Gly
            565                 570                 575

```
Lys Gly Val Pro Gly Val Gly Val Pro Gly Val Gly Val Pro Gly Val
            580                 585                 590

Gly Val Pro Gly Ala Gly Ala Gly Ser Gly Ala Gly Ala Gly Ser Gly
        595                 600                 605

Ala Gly Ala Gly Ser Gly Ala Gly Ala Gly Ser Gly Val Gly Val Pro
    610                 615                 620

Gly Val Gly Val Pro Gly Val Gly Val Pro Gly Val Gly Val Pro Gly
625                 630                 635                 640

Lys Gly Val Pro Gly Val Gly Val Pro Gly Val Gly Val Pro Gly Val
            645                 650                 655

Gly Val Pro Gly Ala Gly Ala Gly Ser Gly Ala Gly Ala Gly Ser Gly
        660                 665                 670

Ala Gly Ala Gly Ser Gly Ala Gly Ala Gly Ser Gly Val Gly Val Pro
    675                 680                 685

Gly Val Gly Val Pro Gly Val Gly Val Pro Gly Val Gly Val Pro Gly
    690                 695                 700

Lys Gly Val Pro Gly Val Gly Val Pro Gly Val Gly Val Pro Gly Val
705                 710                 715                 720

Gly Val Pro Gly Ala Gly Ala Gly Ser Gly Ala Gly Ala Gly Ser Gly
            725                 730                 735

Ala Gly Ala Gly Ser Gly Ala Gly Ala Gly Ser Gly Val Gly Val Pro
        740                 745                 750

Gly Val Gly Val Pro Gly Val Gly Val Pro Gly Val Gly Val Pro Gly
        755                 760                 765

Lys Gly Val Pro Gly Val Gly Val Pro Gly Val Gly Val Pro Gly Val
        770                 775                 780

Gly Val Pro Gly Ala Gly Ala Gly Ser Gly Ala Gly Ala Gly Ser Gly
785                 790                 795                 800

Ala Gly Ala Gly Ser Gly Ala Gly Ala Gly Ser Gly Val Gly Val Pro
            805                 810                 815

Gly Val Gly Val Pro Gly Val Gly Val Pro Gly Val Gly Val Pro Gly
        820                 825                 830

Lys Gly Val Pro Gly Val Gly Val Pro Gly Val Gly Val Pro Gly Val
            835                 840                 845

Gly Val Pro Gly Ala Gly Ala Gly Ser Gly Ala Gly Ala Gly Ser Gly
        850                 855                 860

Ala Gly Ala Met Asp Pro Gly Arg Tyr Gln Asp Leu Arg Ser His His
865                 870                 875                 880

His His His His
```

(2) INFORMATION FOR SEQ ID NO: 16:

(i) SEQUENCE CHARACTERISTICS:
        (A) LENGTH: 1065 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30
```

```
Met Gly Ala His Gly Pro Ala Gly Pro Lys Gly Ala His Gly Pro Ala
         35                  40                  45
Gly Pro Lys Gly Ala Gln Gly Pro Ala Gly Pro Gly Gly Ala Gln Gly
         50                  55                  60
Pro Ala Gly Pro Gly Gly Ala Gln Gly Pro Ala Gly Pro Gly Gly Ala
 65                  70                  75                  80
Gln Gly Pro Ala Gly Pro Gly Gly Ala Gln Gly Pro Ala Gly Pro Gly
                 85                  90                  95
Gly Ala Gln Gly Pro Ala Gly Pro Gly Gly Ala Gln Gly Pro Ala Gly
             100                 105                 110
Pro Gly Gly Ala Gln Gly Pro Ala Gly Pro Gly Gly Ala Gln Gly Pro
             115                 120                 125
Ala Gly Pro Gly Gly Ala Gln Gly Pro Ala Gly Pro Gly Gly Ala Gln
         130                 135                 140
Gly Pro Ala Gly Pro Gly Gly Ala Gln Gly Pro Ala Gly Pro Gly Gly
145                 150                 155                 160
Ala Gln Gly Pro Ala Gly Pro Gly Gly Ala Gln Gly Pro Ala Gly Pro
                165                 170                 175
Gly Gly Ala Gln Gly Pro Ala Gly Pro Gly Gly Ala Gln Gly Pro Ala
             180                 185                 190
Gly Pro Gly Gly Ala Gln Gly Pro Ala Gly Pro Gly Gly Ala Gln Gly
             195                 200                 205
Pro Ala Gly Pro Gly Gly Ala Gln Gly Pro Ala Gly Pro Gly Gly Ala
         210                 215                 220
Gln Gly Pro Ala Gly Pro Gly Gly Ala Gln Gly Pro Ala Gly Pro Gly
225                 230                 235                 240
Gly Ala Gln Gly Pro Ala Gly Pro Gly Gly Ala Gln Gly Pro Ala Gly
                245                 250                 255
Pro Gly Gly Ala Gln Gly Pro Ala Gly Pro Gly Gly Ala His Gly Pro
             260                 265                 270
Ala Gly Pro Lys Gly Ala His Gly Pro Ala Gly Pro Lys Gly Ala His
         275                 280                 285
Gly Pro Ala Gly Pro Lys Gly Ala His Gly Pro Ala Gly Pro Lys Gly
         290                 295                 300
Ala Gln Gly Pro Ala Gly Pro Gly Gly Ala Gln Gly Pro Ala Gly Pro
305                 310                 315                 320
Gly Gly Ala Gln Gly Pro Ala Gly Pro Gly Gly Ala Gln Gly Pro Ala
                325                 330                 335
Gly Pro Gly Gly Ala Gln Gly Pro Ala Gly Pro Gly Gly Ala Gln Gly
             340                 345                 350
Pro Ala Gly Pro Gly Gly Ala Gln Gly Pro Ala Gly Pro Gly Gly Ala
         355                 360                 365
Gln Gly Pro Ala Gly Pro Gly Gly Ala Gln Gly Pro Ala Gly Pro Gly
         370                 375                 380
Gly Ala Gln Gly Pro Ala Gly Pro Gly Gly Ala Gln Gly Pro Ala Gly
385                 390                 395                 400
Pro Gly Gly Ala Gln Gly Pro Ala Gly Pro Gly Gly Ala Gln Gly Pro
                405                 410                 415
Ala Gly Pro Gly Gly Ala Gln Gly Pro Ala Gly Pro Gly Gly Ala Gln
             420                 425                 430
Gly Pro Ala Gly Pro Gly Gly Ala Gln Gly Pro Ala Gly Pro Gly Gly
             435                 440                 445
Ala Gln Gly Pro Ala Gly Pro Gly Gly Ala Gln Gly Pro Ala Gly Pro
```

-continued

```
            450                 455                 460
Gly Gly Ala Gln Gly Pro Ala Gly Pro Gly Ala Gln Gly Pro Ala
465                 470                 475                 480
Gly Pro Gly Gly Ala Gln Gly Pro Ala Gly Pro Gly Gly Ala Gln Gly
                485                 490                 495
Pro Ala Gly Pro Gly Gly Ala Gln Gly Pro Ala Gly Pro Gly Gly Ala
            500                 505                 510
Gln Gly Pro Ala Gly Pro Gly Gly Ala His Gly Pro Ala Gly Pro Lys
            515                 520                 525
Gly Ala His Gly Pro Ala Gly Pro Lys Gly Ala His Gly Pro Ala Gly
            530                 535                 540
Pro Lys Gly Ala His Gly Pro Ala Gly Pro Lys Gly Ala Gln Gly Pro
545                 550                 555                 560
Ala Gly Pro Gly Gly Ala Gln Gly Pro Ala Gly Pro Gly Gly Ala Gln
                565                 570                 575
Gly Pro Ala Gly Pro Gly Gly Ala Gln Gly Pro Ala Gly Pro Gly Gly
            580                 585                 590
Ala Gln Gly Pro Ala Gly Pro Gly Gly Ala Gln Gly Pro Ala Gly Pro
            595                 600                 605
Gly Gly Ala Gln Gly Pro Ala Gly Pro Gly Gly Ala Gln Gly Pro Ala
            610                 615                 620
Gly Pro Gly Gly Ala Gln Gly Pro Ala Gly Pro Gly Gly Ala Gln Gly
625                 630                 635                 640
Pro Ala Gly Pro Gly Gly Ala Gln Gly Pro Ala Gly Pro Gly Gly Ala
                645                 650                 655
Gln Gly Pro Ala Gly Pro Gly Gly Ala Gln Gly Pro Ala Gly Pro Gly
            660                 665                 670
Gly Ala Gln Gly Pro Ala Gly Pro Gly Gly Ala Gln Gly Pro Ala Gly
            675                 680                 685
Pro Gly Gly Ala Gln Gly Pro Ala Gly Pro Gly Gly Ala Gln Gly Pro
            690                 695                 700
Ala Gly Pro Gly Gly Ala Gln Gly Pro Ala Gly Pro Gly Gly Ala Gln
705                 710                 715                 720
Gly Pro Ala Gly Pro Gly Gly Ala Gln Gly Pro Ala Gly Pro Gly Gly
                725                 730                 735
Ala Gln Gly Pro Ala Gly Pro Gly Gly Ala Gln Gly Pro Ala Gly Pro
            740                 745                 750
Gly Gly Ala Gln Gly Pro Ala Gly Pro Gly Gly Ala Gln Gly Pro Ala
            755                 760                 765
Gly Pro Gly Gly Ala His Gly Pro Ala Gly Pro Lys Gly Ala His Gly
            770                 775                 780
Pro Ala Gly Pro Lys Gly Ala His Gly Pro Ala Gly Pro Lys Gly Ala
785                 790                 795                 800
His Gly Pro Ala Gly Pro Lys Gly Ala Gln Gly Pro Ala Gly Pro Gly
                805                 810                 815
Gly Ala Gln Gly Pro Ala Gly Pro Gly Gly Ala Gln Gly Pro Ala Gly
            820                 825                 830
Pro Gly Gly Ala Gln Gly Pro Ala Gly Pro Gly Gly Ala Gln Gly Pro
            835                 840                 845
Ala Gly Pro Gly Gly Ala Gln Gly Pro Ala Gly Pro Gly Gly Ala Gln
            850                 855                 860
Gly Pro Ala Gly Pro Gly Gly Ala Gln Gly Pro Ala Gly Pro Gly Gly
865                 870                 875                 880
```

Ala Gln Gly Pro Ala Gly Pro Gly Gly Ala Gln Gly Pro Ala Gly Pro
                885                 890                 895

Gly Gly Ala Gln Gly Pro Ala Gly Pro Gly Gly Ala Gln Gly Pro Ala
            900                 905                 910

Gly Pro Gly Gly Ala Gln Gly Pro Ala Gly Pro Gly Gly Ala Gln Gly
        915                 920                 925

Pro Ala Gly Pro Gly Gly Ala Gln Gly Pro Ala Gly Pro Gly Gly Ala
    930                 935                 940

Gln Gly Pro Ala Gly Pro Gly Gly Ala Gln Gly Pro Ala Gly Pro Gly
945                 950                 955                 960

Gly Ala Gln Gly Pro Ala Gly Pro Gly Gly Ala Gln Gly Pro Ala Gly
            965                 970                 975

Pro Gly Gly Ala Gln Gly Pro Ala Gly Pro Gly Gly Ala Gln Gly Pro
        980                 985                 990

Ala Gly Pro Gly Gly Ala Gln Gly Pro Ala Gly Pro Gly Gly Ala Gln
    995                 1000                1005

Gly Pro Ala Gly Pro Gly Gly Ala Gln Gly Pro Ala Gly Pro Gly Gly
    1010                1015                1020

Ala His Gly Pro Ala Gly Pro Lys Gly Ala His Gly Pro Ala Gly Pro
1025                1030                1035                1040

Lys Gly Ala Met Asp Pro Gly Arg Tyr Gln Leu Ser Ala Gly Arg Tyr
            1045                1050                1055

His Tyr Gln Leu Val Trp Cys Cys Lys
        1060                1065

(2) INFORMATION FOR SEQ ID NO: 17:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Pro Leu Gly Pro
1

(2) INFORMATION FOR SEQ ID NO: 18:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

Gly Ala Gly Ala Gly Ser Gly Val Gly Val Pro Leu Gly Pro Leu Gly
1               5                   10                  15

Pro Gly Val Gly Val Pro
            20

(2) INFORMATION FOR SEQ ID NO: 19:

(i) SEQUENCE CHARACTERISTICS:
        (A) LENGTH: 24 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 19:

Gly Ala Gly Ala Gly Ser Gly Val Gly Val Pro Gly Phe Phe Val Arg
1               5                   10                  15

Ala Arg Arg Gly Val Gly Val Pro
            20

(2) INFORMATION FOR SEQ ID NO: 20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO: 20:

GATCTTCGAT CTCATCACCA TCACCATCAC TA                                32

(2) INFORMATION FOR SEQ ID NO: 21:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO: 21:

TGCTTAGTGA TGGTGATGGT GATGAGATCG AA                                32

(2) INFORMATION FOR SEQ ID NO: 22:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO: 22:

ATGGCAGCGA AAGGGACCG GTGCCGGCGC AGGTAGCGGA GCCGGTGCGG GCTCAAAAAG    60

GGCTCTGGTG CCTTTCCGCT AAAGTCCTGC CGT                                93

(2) INFORMATION FOR SEQ ID NO: 23:

(i) SEQUENCE CHARACTERISTICS:
        (A) LENGTH: 162 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO: 23:

GGGCTCTGGT GTTGGAGTGC CAGGTGTCGG TGTTCCGGGT GTAGGCGTTC CGGGAGTTGG    60

TGTACCTGGA AAAGGTGTTC CGGGGGTAGG TGTGCCGGGC GTTGGAGTAC CAGGTGTAGG   120

CGTCCCGGGA GCGGGTGCTG GTAGCGGCGC AGGCGCGGGC TC                162

(2) INFORMATION FOR SEQ ID NO: 24:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

```
Gly Ser Gly Val Gly Val Pro Gly Val Gly Val Pro Gly Val Gly Val
 1               5                  10                  15
Pro Gly Val Gly Val Pro Gly Lys Gly Val Pro Gly Val Gly Val Pro
             20                  25                  30
Gly Val Gly Val Pro Gly Val Gly Val Pro Gly Ala Gly Ala Gly Ser
         35                  40                  45
Gly Ala Gly Ala Gly Ser
         50
```

(2) INFORMATION FOR SEQ ID NO: 25:

(i) SEQUENCE CHARACTERISTICS:
        (A) LENGTH: 1002 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 25:

```
Met Asp Pro Val Val Leu Gln Arg Arg Asp Trp Glu Asn Pro Gly Val
 1               5                  10                  15
Thr Gln Leu Asn Arg Leu Ala Ala His Pro Pro Phe Ala Ser Asp Pro
             20                  25                  30
Met Gly Ala Gly Ala Gly Ser Gly Ala Gly Ala Gly Ser Gly Val Gly
         35                  40                  45
Val Pro Gly Val Gly Val Pro Gly Val Gly Val Pro Gly Val Gly Val
     50                  55                  60
Pro Gly Lys Gly Val Pro Gly Val Gly Val Pro Gly Val Gly Val Pro
 65                  70                  75                  80
Gly Val Gly Val Pro Gly Ala Gly Ala Gly Ser Gly Ala Gly Ala Gly
             85                  90                  95
Ser Gly Val Gly Val Pro Gly Val Gly Val Pro Gly Val Gly Val Pro
            100                 105                 110
Gly Val Gly Val Pro Gly Lys Gly Val Pro Gly Val Gly Val Pro Gly
            115                 120                 125
Val Gly Val Pro Gly Val Gly Val Pro Gly Ala Gly Ala Gly Ser Gly
            130                 135                 140
Ala Gly Ala Gly Ser Gly Val Gly Val Pro Gly Val Gly Val Pro Gly
145                 150                 155                 160
Val Gly Val Pro Gly Val Gly Val Pro Gly Lys Gly Val Pro Gly Val
                165                 170                 175
Gly Val Pro Gly Val Gly Val Pro Gly Val Gly Val Pro Gly Ala Gly
            180                 185                 190
Ala Gly Ser Gly Ala Gly Ala Gly Ser Gly Val Gly Val Pro Gly Val
            195                 200                 205
```

-continued

```
Gly Val Pro Gly Val Gly Val Pro Gly Val Gly Val Pro Gly Lys Gly
        210                 215                 220

Val Pro Gly Val Gly Val Pro Gly Val Gly Val Pro Gly Val Gly Val
225                 230                 235                 240

Pro Gly Ala Gly Ala Gly Ser Gly Ala Gly Ala Gly Ser Gly Val Gly
                245                 250                 255

Val Pro Gly Val Gly Val Pro Gly Val Gly Val Pro Gly Val Gly Val
            260                 265                 270

Pro Gly Lys Gly Val Pro Gly Val Gly Val Pro Gly Val Gly Val Pro
        275                 280                 285

Gly Val Gly Val Pro Gly Ala Gly Ala Gly Ser Gly Ala Gly Ala Gly
        290                 295                 300

Ser Gly Val Gly Val Pro Gly Val Gly Val Pro Gly Val Gly Val Pro
305                 310                 315                 320

Gly Val Gly Val Pro Gly Lys Gly Val Pro Gly Val Gly Val Pro Gly
                325                 330                 335

Val Gly Val Pro Gly Val Gly Val Pro Gly Ala Gly Ala Gly Ser Gly
            340                 345                 350

Ala Gly Ala Gly Ser Gly Val Gly Val Pro Gly Val Gly Val Pro Gly
        355                 360                 365

Val Gly Val Pro Gly Val Gly Val Pro Gly Lys Gly Val Pro Gly Val
    370                 375                 380

Gly Val Pro Gly Val Gly Val Pro Gly Val Gly Val Pro Gly Ala Gly
385                 390                 395                 400

Ala Gly Ser Gly Ala Gly Ala Gly Ser Gly Val Gly Val Pro Gly Val
                405                 410                 415

Gly Val Pro Gly Val Gly Val Pro Gly Val Gly Val Pro Gly Lys Gly
            420                 425                 430

Val Pro Gly Val Gly Val Pro Gly Val Gly Val Pro Gly Val Gly Val
        435                 440                 445

Pro Gly Ala Gly Ala Gly Ser Gly Ala Gly Ala Gly Ser Gly Val Gly
    450                 455                 460

Val Pro Gly Val Gly Val Pro Gly Val Gly Val Pro Gly Val Gly Val
465                 470                 475                 480

Pro Gly Lys Gly Val Pro Gly Val Gly Val Pro Gly Val Gly Val Pro
                485                 490                 495

Gly Val Gly Val Pro Gly Ala Gly Ala Gly Ser Gly Ala Gly Ala Gly
            500                 505                 510

Ser Gly Val Gly Val Pro Gly Val Gly Val Pro Gly Val Gly Val Pro
        515                 520                 525

Gly Val Gly Val Pro Gly Lys Gly Val Pro Gly Val Gly Val Pro Gly
    530                 535                 540

Val Gly Val Pro Gly Val Gly Val Pro Gly Ala Gly Ala Gly Ser Gly
545                 550                 555                 560

Ala Gly Ala Gly Ser Gly Val Gly Val Pro Gly Val Gly Val Pro Gly
                565                 570                 575

Val Gly Val Pro Gly Val Gly Val Pro Gly Lys Gly Val Pro Gly Val
            580                 585                 590

Gly Val Pro Gly Val Gly Val Pro Gly Val Gly Val Pro Gly Ala Gly
        595                 600                 605

Ala Gly Ser Gly Ala Gly Ala Gly Ser Gly Val Gly Val Pro Gly Val
    610                 615                 620
```

-continued

```
Gly Val Pro Gly Val Gly Val Pro Gly Val Gly Val Pro Gly Lys Gly
625                 630                 635                 640

Val Pro Gly Val Gly Val Pro Gly Val Gly Val Pro Gly Val Gly Val
            645                 650                 655

Pro Gly Ala Gly Ala Gly Ser Gly Ala Gly Ala Gly Ser Gly Val Gly
        660                 665                 670

Val Pro Gly Val Gly Val Pro Gly Val Gly Val Pro Gly Val Gly Val
            675                 680                 685

Pro Gly Lys Gly Val Pro Gly Val Gly Val Pro Gly Val Gly Val Pro
        690                 695                 700

Gly Val Gly Val Pro Gly Ala Gly Ala Gly Ser Gly Ala Gly Ala Gly
705                 710                 715                 720

Ser Gly Val Gly Val Pro Gly Val Gly Val Pro Gly Val Gly Val Pro
            725                 730                 735

Gly Val Gly Val Pro Gly Lys Gly Val Pro Gly Val Gly Val Pro Gly
        740                 745                 750

Val Gly Val Pro Gly Val Gly Val Pro Gly Ala Gly Ala Gly Ser Gly
            755                 760                 765

Ala Gly Ala Gly Ser Gly Val Gly Val Pro Gly Val Gly Val Pro Gly
770                 775                 780

Val Gly Val Pro Gly Val Gly Val Pro Gly Lys Gly Val Pro Gly Val
785                 790                 795                 800

Gly Val Pro Gly Val Gly Val Pro Gly Val Gly Val Pro Gly Ala Gly
            805                 810                 815

Ala Gly Ser Gly Ala Gly Ala Gly Ser Gly Val Gly Val Pro Gly Val
        820                 825                 830

Gly Val Pro Gly Val Gly Val Pro Gly Val Gly Val Pro Gly Lys Gly
        835                 840                 845

Val Pro Gly Val Gly Val Pro Gly Val Gly Val Pro Gly Val Gly Val
850                 855                 860

Pro Gly Ala Gly Ala Gly Ser Gly Ala Gly Ala Gly Ser Gly Val Gly
865                 870                 875                 880

Val Pro Gly Val Gly Val Pro Gly Val Gly Val Pro Gly Val Gly Val
            885                 890                 895

Pro Gly Lys Gly Val Pro Gly Val Gly Val Pro Gly Val Gly Val Pro
        900                 905                 910

Gly Val Gly Val Pro Gly Ala Gly Ala Gly Ser Gly Ala Gly Ala Gly
        915                 920                 925

Ser Gly Val Gly Val Pro Gly Val Gly Val Pro Gly Val Gly Val Pro
930                 935                 940

Gly Val Gly Val Pro Gly Lys Gly Val Pro Gly Val Gly Val Pro Gly
945                 950                 955                 960

Val Gly Val Pro Gly Val Gly Val Pro Gly Ala Gly Ala Gly Ser Gly
            965                 970                 975

Ala Gly Ala Gly Ser Gly Ala Gly Ala Met Asp Pro Gly Arg Tyr Gln
        980                 985                 990

Asp Leu Arg Ser His His His His His His
        995                 1000
```

(2) INFORMATION FOR SEQ ID NO: 26:

(i) SEQUENCE CHARACTERISTICS:
        (A) LENGTH: 378 amino acids
        (B) TYPE: amino acid
        (C) STRANDEDNESS: single -continued (D) TOPOLOGY: linear (ii) MOLECULE TYPE: protein (xi) SEQUENCE DESCRIPTION: SEQ ID NO: 26:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
        35                  40                  45

Val Pro Gly Val Gly Val Pro Gly Val Gly Val Pro Gly Val Gly Val
    50                  55                  60

Pro Gly Lys Gly Val Pro Gly Val Gly Val Pro Gly Val Gly Val Pro
65                  70                  75                  80

Gly Val Gly Val Pro Gly Ala Gly Ala Gly Ser Gly Ala Gly Ala Gly
                85                  90                  95

Ser Gly Val Gly Val Pro Gly Val Gly Val Pro Gly Val Gly Val Pro
            100                 105                 110

Gly Val Gly Val Pro Gly Lys Gly Val Pro Gly Val Gly Val Pro Gly
        115                 120                 125

Val Gly Val Pro Gly Val Gly Val Pro Gly Ala Gly Ala Gly Ser Gly
    130                 135                 140

Ala Gly Ala Gly Ser Gly Val Gly Val Pro Gly Val Gly Val Pro Gly
145                 150                 155                 160

Val Gly Val Pro Gly Val Gly Val Pro Gly Lys Gly Val Pro Gly Val
                165                 170                 175

Gly Val Pro Gly Val Gly Val Pro Gly Val Gly Val Pro Gly Ala Gly
            180                 185                 190

Ala Gly Ser Gly Ala Gly Ala Gly Ser Gly Val Gly Val Pro Gly Val
        195                 200                 205

Gly Val Pro Gly Val Gly Val Pro Gly Val Gly Val Pro Gly Lys Gly
    210                 215                 220

Val Pro Gly Val Gly Val Pro Gly Val Gly Val Pro Gly Val Gly Val
225                 230                 235                 240

Pro Gly Ala Gly Ala Gly Ser Gly Ala Gly Ala Gly Ser Gly Val Gly
                245                 250                 255

Val Pro Gly Val Gly Val Pro Gly Val Gly Val Pro Gly Val Gly Val
            260                 265                 270

Pro Gly Lys Gly Val Pro Gly Val Gly Val Pro Gly Val Gly Val Pro
        275                 280                 285

Gly Val Gly Val Pro Gly Ala Gly Ala Gly Ser Gly Ala Gly Ala Gly
    290                 295                 300

Ser Gly Val Gly Val Pro Gly Val Gly Val Pro Gly Val Gly Val Pro
305                 310                 315                 320

Gly Val Gly Val Pro Gly Lys Gly Val Pro Gly Val Gly Val Pro Gly
                325                 330                 335

Val Gly Val Pro Gly Val Gly Val Pro Gly Ala Gly Ala Gly Ser Gly
            340                 345                 350

Ala Gly Ala Gly Ser Gly Ala Gly Ala Met Asp Pro Gly Arg Tyr Gln
        355                 360                 365

Asp Leu Arg Ser His His His His His
370                 375
```

(2) INFORMATION FOR SEQ ID NO: 27:

(i) SEQUENCE CHARACTERISTICS:
       (A) LENGTH: 141 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "synthetic"

(xi) SEQUENCE DESCRIPTION: SEQ ID NO: 27:

```
ATGGCAGCGA AAGGGGACCG CCGGTGCGGG CTCTGGTGTT GGAGTGCCGC TGGGTCCTCT    60

TGGCCCAGGT GTCGGTGTTC CGGGTGTAGG CGTTCCGGGA GTTGGTGTAC CTGGAAAAGG   120

TTTCCGCTAA AGTCCTGCCG T                                             141
```

(2) INFORMATION FOR SEQ ID NO: 28:

(i) SEQUENCE CHARACTERISTICS:
       (A) LENGTH: 181 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "synthetic"

(xi) SEQUENCE DESCRIPTION: SEQ ID NO: 28:

```
GGGCTCTGGT GTTGGAGTGC CGCTGGGTCC TCTTGGCCCA GGTGTCGGTG TTCCGGGTGT    60

AGGCGTTCCG GGAGTTGGTG TACCTGGAAA AGGTGTTCCG GGGGTAGGTG TGCCGGGCGT   120

TGGAGTACCA GGTGTAGGCG TCCCGGGAGC GGGTGCTGGT AGCGGCGCAG GCGCGGGCTC   180

T                                                                   181
```

(2) INFORMATION FOR SEQ ID NO: 29:

(i) SEQUENCE CHARACTERISTICS:
       (A) LENGTH: 60 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 29:

```
Gly Ser Gly Val Gly Val Pro Leu Gly Pro Leu Gly Pro Gly Val Gly
 1               5                  10                  15

Val Pro Gly Val Gly Val Pro Gly Val Gly Val Pro Gly Lys Gly Val
            20                  25                  30

Pro Gly Val Gly Val Pro Gly Val Gly Val Pro Gly Val Gly Val Pro
        35                  40                  45

Gly Ala Gly Ala Gly Ser Gly Ala Gly Ala Gly Ser
    50                  55                  60
```

(2) INFORMATION FOR SEQ ID NO: 30:

(i) SEQUENCE CHARACTERISTICS:
       (A) LENGTH: 936 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 30:

-continued

```
Met Asp Pro Val Val Leu Gln Arg Arg Asp Trp Glu Asn Pro Gly Val
 1               5                  10                 15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
            35                  40                  45

Val Pro Leu Gly Pro Leu Gly Pro Gly Val Gly Val Pro Gly Val Gly
 50                  55                  60

Val Pro Gly Val Gly Val Pro Gly Lys Gly Val Pro Gly Val Gly Val
 65                  70                  75                  80

Pro Gly Val Gly Val Pro Gly Val Gly Val Pro Gly Ala Gly Ala Gly
                 85                  90                  95

Ser Gly Ala Gly Ala Gly Ser Gly Val Gly Val Pro Leu Gly Pro Leu
                100                 105                 110

Gly Pro Gly Val Gly Val Pro Gly Val Gly Val Pro Gly Val Gly Val
                115                 120                 125

Pro Gly Lys Gly Val Pro Gly Val Gly Val Pro Gly Val Gly Val Pro
            130                 135                 140

Gly Val Gly Val Pro Gly Ala Gly Ala Gly Ser Gly Ala Gly Ala Gly
145                 150                 155                 160

Ser Gly Val Gly Val Pro Leu Gly Pro Leu Gly Pro Gly Val Gly Val
                165                 170                 175

Pro Gly Val Gly Val Pro Gly Val Gly Val Pro Gly Lys Gly Val Pro
                180                 185                 190

Gly Val Gly Val Pro Gly Val Gly Val Pro Gly Val Gly Val Pro Gly
            195                 200                 205

Ala Gly Ala Gly Ser Gly Ala Gly Ala Gly Ser Gly Val Gly Val Pro
            210                 215                 220

Leu Gly Pro Leu Gly Pro Gly Val Gly Val Pro Gly Val Gly Val Pro
225                 230                 235                 240

Gly Val Gly Val Pro Gly Lys Gly Val Pro Gly Val Gly Val Pro Gly
                245                 250                 255

Val Gly Val Pro Gly Val Gly Val Pro Gly Ala Gly Ala Gly Ser Gly
            260                 265                 270

Ala Gly Ala Gly Ser Gly Val Gly Val Pro Leu Gly Pro Leu Gly Pro
            275                 280                 285

Gly Val Gly Val Pro Gly Val Gly Val Pro Gly Val Gly Val Pro Gly
            290                 295                 300

Lys Gly Val Pro Gly Val Gly Val Pro Gly Val Gly Val Pro Gly Val
305                 310                 315                 320

Gly Val Pro Gly Ala Gly Ala Gly Ser Gly Ala Gly Ala Gly Ser Gly
            325                 330                 335

Val Gly Val Pro Leu Gly Pro Leu Gly Pro Gly Val Gly Val Pro Gly
            340                 345                 350

Val Gly Val Pro Gly Val Gly Val Pro Gly Lys Gly Val Pro Gly Val
            355                 360                 365

Gly Val Pro Gly Val Gly Val Pro Gly Val Gly Val Pro Gly Ala Gly
            370                 375                 380

Ala Gly Ser Gly Ala Gly Ala Gly Ser Gly Val Gly Val Pro Leu Gly
385                 390                 395                 400

Pro Leu Gly Pro Gly Val Gly Val Pro Gly Val Gly Val Pro Gly Val
                405                 410                 415

Gly Val Pro Gly Lys Gly Val Pro Gly Val Gly Val Pro Gly Val Gly
```

```
                420              425              430
Val Pro Gly Val Gly Val Pro Gly Ala Gly Ala Gly Ser Gly Ala Gly
            435              440              445
Ala Gly Ser Gly Val Gly Val Pro Leu Gly Pro Leu Gly Pro Gly Val
            450              455              460
Gly Val Pro Gly Val Gly Val Pro Gly Val Gly Val Pro Gly Lys Gly
465              470              475              480
Val Pro Gly Val Gly Val Pro Gly Val Gly Val Pro Gly Val Gly Val
                485              490              495
Pro Gly Ala Gly Ala Gly Ser Gly Ala Gly Ala Gly Ser Gly Val Gly
                500              505              510
Val Pro Leu Gly Pro Leu Gly Pro Gly Val Gly Val Pro Gly Val Gly
                515              520              525
Val Pro Gly Val Gly Val Pro Gly Lys Gly Val Pro Gly Val Gly Val
                530              535              540
Pro Gly Val Gly Val Pro Gly Val Gly Val Pro Gly Ala Gly Ala Gly
545              550              555              560
Ser Gly Ala Gly Ala Gly Ser Gly Val Gly Val Pro Leu Gly Pro Leu
            565              570              575
Gly Pro Gly Val Gly Val Pro Gly Val Gly Val Pro Gly Val Gly Val
            580              585              590
Pro Gly Lys Gly Val Pro Gly Val Gly Val Pro Gly Val Gly Val Pro
            595              600              605
Gly Val Gly Val Pro Gly Ala Gly Ala Gly Ser Gly Ala Gly Ala Gly
610              615              620
Ser Gly Val Gly Val Pro Leu Gly Pro Leu Gly Pro Gly Val Gly Val
625              630              635              640
Pro Gly Val Gly Val Pro Gly Val Gly Val Pro Gly Lys Gly Val Pro
            645              650              655
Gly Val Gly Val Pro Gly Val Gly Val Pro Gly Val Gly Val Pro Gly
            660              665              670
Ala Gly Ala Gly Ser Gly Ala Gly Ala Gly Ser Gly Val Gly Val Pro
            675              680              685
Leu Gly Pro Leu Gly Pro Gly Val Gly Val Pro Gly Val Gly Val Pro
            690              695              700
Gly Val Gly Val Pro Gly Lys Gly Val Pro Gly Val Gly Val Pro Gly
705              710              715              720
Val Gly Val Pro Gly Val Gly Val Pro Gly Ala Gly Ala Gly Ser Gly
                725              730              735
Ala Gly Ala Gly Ser Gly Val Gly Val Pro Leu Gly Pro Leu Gly Pro
                740              745              750
Gly Val Gly Val Pro Gly Val Gly Val Pro Gly Val Gly Val Pro Gly
                755              760              765
Lys Gly Val Pro Gly Val Gly Val Pro Gly Val Gly Val Pro Gly Val
            770              775              780
Gly Val Pro Gly Ala Gly Ala Gly Ser Gly Ala Gly Ala Gly Ser Gly
785              790              795              800
Val Gly Val Pro Leu Gly Pro Leu Gly Pro Gly Val Gly Val Pro Gly
                805              810              815
Val Gly Val Pro Gly Val Gly Val Pro Gly Lys Gly Val Pro Gly Val
            820              825              830
Gly Val Pro Gly Val Gly Val Pro Gly Val Gly Val Pro Gly Ala Gly
            835              840              845
```

Ala Gly Ser Gly Ala Gly Ala Gly Ser Gly Val Gly Val Pro Leu Gly
            850                 855                 860

Pro Leu Gly Pro Gly Val Gly Val Pro Gly Val Gly Val Pro Gly Val
865                 870                 875                 880

Gly Val Pro Gly Lys Gly Val Pro Gly Val Gly Val Pro Gly Val Gly
                    885                 890                 895

Val Pro Gly Val Gly Val Pro Gly Ala Gly Ala Gly Ser Gly Ala Gly
            900                 905                 910

Ala Gly Ser Gly Ala Gly Ala Met Asp Pro Gly Arg Tyr Gln Asp Leu
            915                 920                 925

Arg Ser His His His His His His
930                 935

(2) INFORMATION FOR SEQ ID NO: 31:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO: 31:

```
ATGGCAGCGA AAGGGGACCG CCGGTGCGGG CTCTGGTGTT GGAGTGCCAG GCTTCTTTGT      60

ACGTGCACGC CGTGGTGTCG GTGTTCCGGG TGTAGGCGTT CCGGGAGTTG GTGTACCTGG     120

AAAAGGTTTC CGCTAAAGTC CTGCCGT                                        147
```

(2) INFORMATION FOR SEQ ID NO: 32:

(i) SEQUENCE CHARACTERISTICS:
        (A) LENGTH: 186 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(xi) SEQUENCE DESCRIPTION: SEQ ID NO: 32:

```
GGGCTCTGGT GTTGGAGTGC CAGGCTTCTT TGTACGTGCA CGCCGTGGTG TCGGTGTTCC      60

GGGTGTAGGC GTTCCGGGAG TTGGTGTACC TGGAAAAGGT GTTCCGGGGG TAGGTGTGCC     120

GGGCGTTGGA GTACCAGGTG TAGGCGTCCC GGGAGCGGGT GCTGGTAGCG GCGCAGGCGC     180

GGGCTC                                                               186
```

(2) INFORMATION FOR SEQ ID NO: 33:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Gly Ser Gly Val Gly Val Pro Gly Phe Phe Val Arg Ala Arg Arg Gly
1               5                   10                  15

Val Gly Val Pro Gly Val Gly Val Pro Gly Val Gly Val Pro Gly Lys
            20                  25                  30

```
Gly Val Pro Gly Val Gly Val Pro Gly Val Gly Val Pro Gly Val Gly
            35                  40                  45

Val Pro Gly Ala Gly Ala Gly Ser Gly Ala Gly Ala Gly Ser
        50                  55                  60

(2) INFORMATION FOR SEQ ID NO: 34:

(i) SEQUENCE CHARACTERISTICS:
        (A) LENGTH: 966 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 34:

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
            35                  40                  45

Val Pro Gly Phe Phe Val Arg Ala Arg Arg Gly Val Gly Val Pro Gly
        50                  55                  60

Val Gly Val Pro Gly Val Gly Val Pro Gly Lys Gly Val Pro Gly Val
65                  70                  75                  80

Gly Val Pro Gly Val Gly Val Pro Gly Val Gly Val Pro Gly Ala Gly
                85                  90                  95

Ala Gly Ser Gly Ala Gly Ala Gly Ser Gly Val Gly Val Pro Gly Phe
            100                 105                 110

Phe Val Arg Ala Arg Arg Gly Val Gly Val Pro Gly Val Gly Val Pro
            115                 120                 125

Gly Val Gly Val Pro Gly Lys Gly Val Pro Gly Val Gly Val Pro Gly
        130                 135                 140

Val Gly Val Pro Gly Val Gly Val Pro Gly Ala Gly Ala Gly Ser Gly
145                 150                 155                 160

Ala Gly Ala Gly Ser Gly Val Gly Val Pro Gly Phe Phe Val Arg Ala
                165                 170                 175

Arg Arg Gly Val Gly Val Pro Gly Val Gly Val Pro Gly Val Gly Val
            180                 185                 190

Pro Gly Lys Gly Val Pro Gly Val Gly Val Pro Gly Val Gly Val Pro
        195                 200                 205

Gly Val Gly Val Pro Gly Ala Gly Ala Gly Ser Gly Ala Gly Ala Gly
        210                 215                 220

Ser Gly Val Gly Val Pro Gly Phe Phe Val Arg Ala Arg Arg Gly Val
225                 230                 235                 240

Gly Val Pro Gly Val Gly Val Pro Gly Val Gly Val Pro Gly Lys Gly
                245                 250                 255

Val Pro Gly Val Gly Val Pro Gly Val Gly Val Pro Gly Val Gly Val
            260                 265                 270

Pro Gly Ala Gly Ala Gly Ser Gly Ala Gly Ala Gly Ser Gly Val Gly
        275                 280                 285

Val Pro Gly Phe Phe Val Arg Ala Arg Arg Gly Val Gly Val Pro Gly
        290                 295                 300

Val Gly Val Pro Gly Val Gly Val Pro Gly Lys Gly Val Pro Gly Val
305                 310                 315                 320
```

-continued

Gly Val Pro Gly Val Gly Val Pro Gly Val Gly Val Pro Gly Ala Gly
                325                 330                 335

Ala Gly Ser Gly Ala Gly Ala Gly Ser Gly Val Gly Val Pro Gly Phe
            340                 345                 350

Phe Val Arg Ala Arg Arg Gly Val Gly Val Pro Gly Val Gly Val Pro
            355                 360                 365

Gly Val Gly Val Pro Gly Lys Gly Val Pro Gly Val Gly Val Pro Gly
        370                 375                 380

Val Gly Val Pro Gly Val Gly Val Pro Gly Ala Gly Ala Gly Ser Gly
385                 390                 395                 400

Ala Gly Ala Gly Ser Gly Val Gly Val Pro Gly Phe Phe Val Arg Ala
            405                 410                 415

Arg Arg Gly Val Gly Val Pro Gly Val Gly Val Pro Gly Val Gly Val
            420                 425                 430

Pro Gly Lys Gly Val Pro Gly Val Gly Val Pro Gly Val Gly Val Pro
        435                 440                 445

Gly Val Gly Val Pro Gly Ala Gly Ala Gly Ser Gly Ala Gly Ala Gly
        450                 455                 460

Ser Gly Val Gly Val Pro Gly Phe Phe Val Arg Ala Arg Arg Gly Val
465                 470                 475                 480

Gly Val Pro Gly Val Gly Val Pro Gly Val Gly Val Pro Gly Lys Gly
            485                 490                 495

Val Pro Gly Val Gly Val Pro Gly Val Gly Val Pro Gly Val Gly Val
            500                 505                 510

Pro Gly Ala Gly Ala Gly Ser Gly Ala Gly Ala Gly Ser Gly Val Gly
        515                 520                 525

Val Pro Gly Phe Phe Val Arg Ala Arg Arg Gly Val Gly Val Pro Gly
        530                 535                 540

Val Gly Val Pro Gly Val Gly Val Pro Gly Lys Gly Val Pro Gly Val
545                 550                 555                 560

Gly Val Pro Gly Val Gly Val Pro Gly Val Gly Val Pro Gly Ala Gly
            565                 570                 575

Ala Gly Ser Gly Ala Gly Ala Gly Ser Gly Val Gly Val Pro Gly Phe
            580                 585                 590

Phe Val Arg Ala Arg Arg Gly Val Gly Val Pro Gly Val Gly Val Pro
        595                 600                 605

Gly Val Gly Val Pro Gly Lys Gly Val Pro Gly Val Gly Val Pro Gly
        610                 615                 620

Val Gly Val Pro Gly Val Gly Val Pro Gly Ala Gly Ala Gly Ser Gly
625                 630                 635                 640

Ala Gly Ala Gly Ser Gly Val Gly Val Pro Gly Phe Phe Val Arg Ala
            645                 650                 655

Arg Arg Gly Val Gly Val Pro Gly Val Gly Val Pro Gly Val Gly Val
            660                 665                 670

Pro Gly Lys Gly Val Pro Gly Val Gly Val Pro Gly Val Gly Val Pro
        675                 680                 685

Gly Val Gly Val Pro Gly Ala Gly Ala Gly Ser Gly Ala Gly Ala Gly
        690                 695                 700

Ser Gly Val Gly Val Pro Gly Phe Phe Val Arg Ala Arg Arg Gly Val
705                 710                 715                 720

Gly Val Pro Gly Val Gly Val Pro Gly Val Gly Val Pro Gly Lys Gly
            725                 730                 735

-continued

```
Val Pro Gly Val Gly Val Pro Gly Val Pro Gly Val Gly Val
            740             745             750

Pro Gly Ala Gly Ala Gly Ser Gly Ala Gly Ala Gly Ser Gly Val Gly
            755             760             765

Val Pro Gly Phe Phe Val Arg Ala Arg Arg Gly Val Gly Val Pro Gly
            770             775             780

Val Gly Val Pro Gly Val Gly Val Pro Gly Lys Gly Val Pro Gly Val
785             790             795             800

Gly Val Pro Gly Val Gly Val Pro Gly Val Gly Val Pro Gly Ala Gly
            805             810             815

Ala Gly Ser Gly Ala Gly Ala Gly Ser Gly Val Gly Val Pro Gly Phe
            820             825             830

Phe Val Arg Ala Arg Arg Gly Val Gly Val Pro Gly Val Gly Val Pro
            835             840             845

Gly Val Gly Val Pro Gly Lys Gly Val Pro Gly Val Gly Val Pro Gly
850             855             860

Val Gly Val Pro Gly Val Gly Val Pro Gly Ala Gly Ala Gly Ser Gly
865             870             875             880

Ala Gly Ala Gly Ser Gly Val Gly Val Pro Gly Phe Phe Val Arg Ala
            885             890             895

Arg Arg Gly Val Gly Val Pro Gly Val Gly Val Pro Gly Val Gly Val
            900             905             910

Pro Gly Lys Gly Val Pro Gly Val Gly Val Pro Gly Val Gly Val Pro
            915             920             925

Gly Val Gly Val Pro Gly Ala Gly Ala Gly Ser Gly Ala Gly Ala Gly
            930             935             940

Ser Gly Ala Gly Ala Met Asp Pro Gly Arg Tyr Gln Asp Leu Arg Ser
945             950             955             960

His His His His His His
                965
```

(2) INFORMATION FOR SEQ ID NO: 35:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

```
Arg Gly Arg Gly Arg Gly Lys Gly Lys Gly Lys
1               5               10
```